United States Patent
Oh et al.

(10) Patent No.: US 12,070,356 B2
(45) Date of Patent: Aug. 27, 2024

(54) MEDICAL IMAGING APPARATUS TO AUTOMATICALLY DETERMINE PRESENCE OF AN ABNORMALITY INCLUDING A DETERMINATION TO TRANSMIT AN ASSISTANCE IMAGE AND A CLASSIFIED ABNORMALITY STAGE

(71) Applicant: SAMSUNG ELECTRONICS CO., LTD., Suwon-si (KR)

(72) Inventors: Hyun-hwa Oh, Hwaseong-si (KR); Dong-jae Lee, Seoul (KR); Se-min Kim, Ansan-si (KR); Jeong-yong Song, Bucheon-si (KR); Hyun-jung Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 539 days.

(21) Appl. No.: 16/174,585

(22) Filed: Oct. 30, 2018

(65) Prior Publication Data

US 2019/0125306 A1 May 2, 2019

(30) Foreign Application Priority Data

Oct. 30, 2017 (KR) .................. 10-2017-0142565
Oct. 29, 2018 (KR) .................. 10-2018-0129779

(51) Int. Cl.
*A61B 8/00* (2006.01)
*A61B 5/00* (2006.01)
(Continued)

(52) U.S. Cl.
CPC ............ *A61B 8/463* (2013.01); *A61B 5/0013* (2013.01); *A61B 6/463* (2013.01); *A61B 6/563* (2013.01);
(Continued)

(58) Field of Classification Search
CPC ....... A61B 8/463; A61B 5/0013; A61B 8/483; A61B 6/563; A61B 6/463; A61B 6/5205;
(Continued)

(56) References Cited

U.S. PATENT DOCUMENTS 7,492,933 B2 2/2009 Krishnan
7,668,352 B2 2/2010 Tecotzky et al.
(Continued)

FOREIGN PATENT DOCUMENTS

CN 101604458 A 12/2009
JP 2006-55507 A 3/2006
(Continued)

OTHER PUBLICATIONS

Communication dated Apr. 11, 2022 issued by the European Patent Office in application No. 18203288.8.
Communication dated Jan. 24, 2019, from the European Patent Office in counterpart European Application No. 18203288.8.
(Continued)

*Primary Examiner* — Christopher Koharski
*Assistant Examiner* — Richmond J Van Winter
(74) *Attorney, Agent, or Firm* — Sughrue Mion, PLLC

(57) ABSTRACT

A medical image transmitting method includes obtaining a medical image generated by imaging an object; performing a first determination to determine whether the object has an abnormality, based on the medical image; performing a second determination to determine, based on the first determination, whether to transmit at least one assistance image associated with the medical image; and when the object has no abnormalities, transmitting, to an external apparatus, the medical image, thereby minimizing a data processing amount and a data transmission amount.

14 Claims, 21 Drawing Sheets

(51) Int. Cl.
  *A61B 6/00* (2006.01)
  *A61B 6/46* (2024.01)
  *A61B 8/08* (2006.01)
  *G06T 7/00* (2017.01)
  *G16H 30/40* (2018.01)
  *G16H 40/63* (2018.01)
  *G16H 50/20* (2018.01)
  *A61B 1/00* (2006.01)
  *A61B 1/045* (2006.01)
  *A61B 5/055* (2006.01)
  *G06T 5/70* (2024.01)

(52) U.S. Cl.
  CPC ........... *G06T 7/0012* (2013.01); *G16H 30/40* (2018.01); *G16H 40/63* (2018.01); *G16H 50/20* (2018.01); *A61B 1/00016* (2013.01); *A61B 1/045* (2013.01); *A61B 5/055* (2013.01); *A61B 6/5205* (2013.01); *A61B 6/5217* (2013.01); *A61B 8/08* (2013.01); *A61B 8/466* (2013.01); *A61B 8/483* (2013.01); *G06T 5/70* (2024.01); *G06T 2207/10081* (2013.01); *G06T 2207/10088* (2013.01); *G06T 2207/10116* (2013.01); *G06T 2207/10132* (2013.01); *G06T 2207/20084* (2013.01); *G06T 2207/30004* (2013.01); *G06T 2207/30061* (2013.01); *G06T 2207/30096* (2013.01)

(58) Field of Classification Search
  CPC .............. A61B 6/5217; A61B 1/00016; A61B 1/045; A61B 5/055; A61B 8/08; A61B 8/466; G06T 7/0012; G06T 2207/10116; G06T 2207/30061; G06T 2207/30096; G06T 2207/20084; G06T 5/002; G06T 2207/10081; G06T 2207/10088; G06T 2207/10132; G06T 2207/30004; G16H 50/20; G16H 40/63; G16H 30/40; G16H 15/00; G16H 30/00; G16H 30/20
  See application file for complete search history.

(56) References Cited

U.S. PATENT DOCUMENTS

| | | | |
|---|---|---|---|
| 9,959,622 | B2 | 5/2018 | Kim et al. |
| 10,140,421 | B1 | 11/2018 | Bernard et al. |
| 2009/0309874 | A1 | 12/2009 | Salganicoff et al. |
| 2011/0144482 | A1* | 6/2011 | Sendai .................. G06T 7/0012 600/425 |
| 2012/0250961 | A1* | 10/2012 | Iwasaki .................. G16H 15/00 382/128 |
| 2013/0257910 | A1* | 10/2013 | Park ........................ G06F 18/00 382/128 |
| 2015/0332454 | A1* | 11/2015 | Yin .......................... G06T 19/20 382/131 |
| 2016/0027175 | A1* | 1/2016 | Kim ....................... G06T 7/0016 382/131 |
| 2017/0091928 | A1* | 3/2017 | Von Berg ............... A61B 6/505 |
| 2017/0270695 | A1* | 9/2017 | Avinash ................. A61B 6/507 |
| 2018/0341747 | A1* | 11/2018 | Bernard ................. A61B 5/002 |

FOREIGN PATENT DOCUMENTS

| | | |
|---|---|---|
| JP | 2011-101759 A | 5/2011 |
| JP | 2015-158776 A | 9/2015 |
| KR | 10-1241060 B1 | 3/2013 |
| KR | 10-2016-0012038 A | 2/2016 |
| WO | 2010/034968 A8 | 4/2010 |

OTHER PUBLICATIONS

Communication dated Oct. 27, 2023 by the Korean Intellectual Property Office for Korean Patent Application No. 10-2018-0129779.
Communication dated Sep. 28, 2023 by the China National Intellectual Property Administration for Chinese Patent Application No. 201811275981.5.
Office Action dated Mar. 9, 2024, issued by the National Intellectual Property Administration, PRC in Chinese Application No. 201811275981.5.
Communication dated May 18, 2024 from the State Intellectual Property Office of PR of China in CN 201811275981.5.
Communication issued on Jul. 1, 2024, by the European Patent Office in counterpart European Application No. 18203288.8.

* cited by examiner

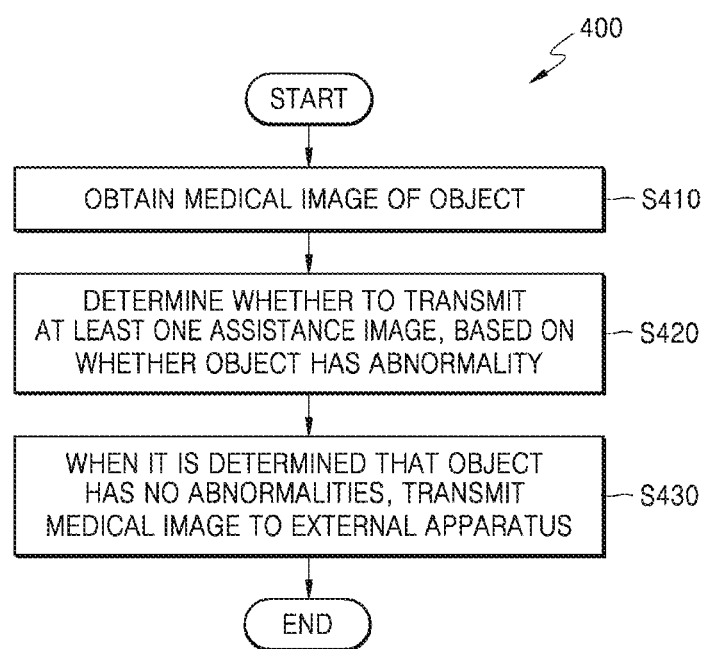

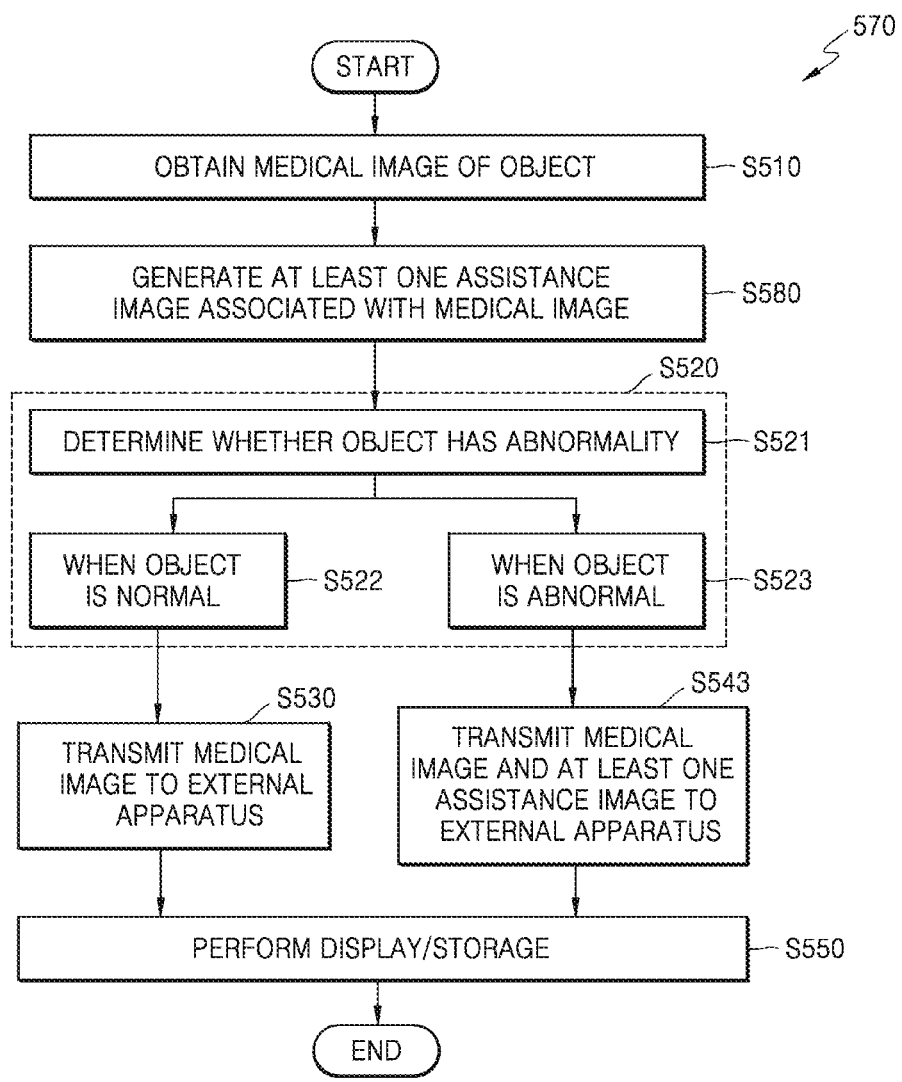

MEDICAL IMAGING APPARATUS TO AUTOMATICALLY DETERMINE PRESENCE OF AN ABNORMALITY INCLUDING A DETERMINATION TO TRANSMIT AN ASSISTANCE IMAGE AND A CLASSIFIED ABNORMALITY STAGE

CROSS-REFERENCE TO RELATED APPLICATIONS

This application is based on and claims priority under 35 U.S.C. § 119 to Korean Patent Application No. 10-2017-0142565, filed on Oct. 30, 2017, and Korean Patent Application No. 10-2018-0129779 filed on Oct. 29, 2018, in the Korean Intellectual Property Office, the disclosures of which are incorporated by reference herein in their entirety.

BACKGROUND

1. Field

The disclosure relates to a method and apparatus for transmitting at least one of a medical image and a read assistance image associated with the medical image to an external apparatus.

More particularly, the disclosure relates to a method and apparatus for obtaining a medical image, generating at least one read assistance image associated with the obtained medical image, based on the obtained medical image, and transmitting at least one of the medical image and the at least one read assistance image to an external apparatus.

2. Description of the Related Art

Medical imaging apparatuses are used for capturing images of an internal structure of an object such as a patient, or a part of a patient, such as an internal organ. Medical imaging apparatuses are noninvasive examination apparatuses that capture and process images of the structural details of a human body, such as internal tissues thereof, or fluid flow within a human body, and provide the processed images to a user. A user, such as a doctor or another type of healthcare provider, may diagnose a health state and a disease of a patient by using a medical image output from a medical imaging apparatus.

Examples of medical imaging apparatuses include X-ray apparatuses for obtaining an image by radiating an X-ray to an object and sensing an X-ray transmitted by the object, magnetic resonance imaging (MRI) apparatuses for providing a magnetic resonance (MR) image, computed tomography (CT) apparatuses, and ultrasound diagnostic apparatuses.

SUMMARY

Provided are a medical image transmitting method capable of minimizing an increase in a memory capacity, an increase in a data processing amount, and an increase in a data transmission amount that occur when a medical image and at least one read assistance image are transmitted to an external apparatus, and a medical imaging apparatus performing the medical image transmitting method.

In detail, provided are a medical image transmitting method capable of minimizing an increase in a memory capacity, an increase in a data processing amount, and an increase in a data transmission amount that occur when an X-ray image and at least one read assistance image produced based on the X-ray image are transmitted to an external apparatus, and a medical imaging apparatus performing the medical image transmitting method.

Provided are a medical image transmitting method enabling a doctor to more conveniently determine whether an abnormality has been generated in an object, by using a medical image, and a medical imaging apparatus performing the medical image transmitting method.

Additional aspects will be set forth in part in the description which follows and, in part, will be apparent from the description, or may be learned by practice of the presented embodiments.

In accordance with an aspect of the disclosure, a medical image transmitting method includes obtaining a medical image generated by imaging an object; performing a first determination to determine whether the object has an abnormality, based on the medical image, and performing a second determination to determine, based on the first determination, whether to transmit at least one assistance image associated with the medical image; and, when the object has no abnormalities, transmitting, to an external apparatus, the medical image and not the at least one assistance image.

The transmitting, to the external apparatus, of the medical image and not the at least one assistance image may include, when the object has no abnormalities, not generating the at least one assistance image associated with the medical image and transmitting the medical image to the external apparatus.

The medical image transmitting method according to an embodiment may further include, when the object has an abnormality, generating at least one read assistance image associated with the medical image and transmitting the medical image and the at least one read assistance image to the external apparatus.

The medical image transmitting method may further include, when the object has an abnormality, generating the at least two assistance images associated with the medical image; and arranging the at least two assistance images in a certain order, based on characteristics of an abnormal part of the object, and transmitting the medical image and the at least two assistance images arranged in the certain order to the external apparatus.

The transmitting of the medical image and not the at least one assistance image to the external apparatus may include, when the object has no abnormalities, attaching, to the medical image, a normality mark indicating that the object is normal, and transmitting, to the external apparatus, the medical image to which the normality mark has been attached.

The transmitting, to the external apparatus, of the medical image and not the at least one read assistance image may further include, when the object has an abnormality, attaching, to the medical image, an abnormality mark indicating that the object is abnormal, and transmitting, to the external apparatus, the medical image to which the abnormality mark has been attached.

The medical image transmitting method may further include, when the object has a lesion, determining a type of a assistance image to be generated, based on characteristics of the lesion, and generating the at least one assistance image according to the determined type; and transmitting the medical image and the at least one assistance image to the external apparatus.

The medical image transmitting method may further include, when the object has no abnormalities, generating data corresponding to a first user interface (UI) screen including the medical image and not the at least one assistance image; and when the object has an abnormality, generating data corresponding to a second UI screen including the medical image and the at least one assistance image.

The medical image transmitting method according to an embodiment may further include displaying the first UI screen or the second UI screen on a display.

The medical image transmitting method may further include, when the object has no abnormalities, transmitting the data corresponding to the first UI screen to the external apparatus; and when the object has an abnormality, transmitting the data corresponding to the second UI screen to the external apparatus.

The first determination may include determining whether the object has an abnormality, via learning operations based on a deep neural network (DNN).

The medical image may include an X-ray image, and the external apparatus may include at least one of a picture archiving communications system (PACS) server, a PACS viewer, and a workstation for controlling a medical imaging apparatus that performs medical image capturing.

In accordance with another aspect of the disclosure, a medical imaging apparatus includes a controller configured to obtain a medical image generated by imaging an object, performing a first determination to determine whether the object has an abnormality, performing a second determination to determine, based on the first determination, whether to transmit at least one assistance image associated with the medical image, and, when the object has no abnormalities, transmit, to an external apparatus, the medical image and not the assistance image; and a communicator configured to transmit the medical image to the external apparatus under the control of the controller.

When the object has no abnormalities, the controller may be further configured to attach, to the medical image, a normality mark indicating that the object is normal, and transmit, to the external apparatus, the medical image to which the normality mark has been attached.

When the object has an abnormality, the controller may be further configured to attach, to the medical image, an abnormality mark indicating that the object is abnormal, and transmit, to the external apparatus, the medical image to which the abnormality mark has been attached.

When the object has an abnormality, the controller may be further configured to generate the at least two assistance images associated with the medical image, arrange the at least two assistance images in a certain order, based on characteristics of an abnormal part of the object, and control the medical image and the at least two assistance images arranged in the certain order to be transmitted to the external apparatus.

When the object has a lesion, the controller may be further configured to determine a type of a assistance image that is to be generated, based on a type of the lesion, generate the at least one assistance image according to the determined type, and transmit the medical image and the at least one assistance image to the external apparatus.

When the object has no abnormalities, the controller may be further configured to control generation of data corresponding to a first UI screen including the medical image and not the at least one assistance image. When the object has an abnormality, the controller may be further configured to control generation of data corresponding to a second UI screen including the medical image and the at least one assistance image. The controller may be further configured to control transmitting of the data corresponding to the first UI screen or the data corresponding to the second UI screen to the external apparatus.

When the object has no abnormalities, the controller may be further configured to control generation of data corresponding to a first UI screen including the medical image and not the at least one assistance image. When the object has an abnormality, the controller may be further configured to control generation of data corresponding to a second UI screen including the medical image and the at least one assistance image. The medical imaging apparatus may further include a display configured to display the first UI screen or the second UI screen under the control of the controller.

The medical imaging apparatus may further include a deep neural network (DNN) processor configured to perform learning operations via a DNN. The controller may be further configured to determine whether the object has an abnormality, via the learning operations based on the DNN.

The medical imaging apparatus may further include an X-ray radiator configured to radiate an X-ray to the object. The controller may be further configured to control the X-ray radiator to obtain the medical image.

The at least one assistance image may be generated based on an analysis of the medical image, and the at least one assistance image may include a lesion and a marking indicating a presence of the lesion.

In accordance with another aspect of the disclosure, a medical imaging apparatus includes a communicator; and a controller configured to obtain a medical image generated by imaging an object, analyze the medical image to determine whether an abnormality is present or the abnormality is not present in the medical image, if the abnormality is present in the medical image, generate at least one assistance image based on the medical image in an assistance image generation operation, and control the communicator to transmit both the medical image and the at least one assistance image to an external apparatus, and if the abnormality is not present in the medical image, not generate the at least one assistance image by skipping the assistance image generation operation and control the communicator to transmit only the medical image, to the external apparatus, wherein the at least one assistance image comprises a marking indicating a presence of the abnormality.

The controller may obtain the medical image by receiving the medical image from an external apparatus.

The medical imaging apparatus may include an X-ray generator and an X-ray detector, and the controller images the object and obtains the medical image by activating the X-ray generator and detecting signals generated by the X-ray detector.

The controller may generate a plurality of assistance images if an abnormality is present, and each assistance image is based on the medical image.

In accordance with another aspect of the disclosure, a medical imaging apparatus includes a display; and a controller configured to obtain a medical image generated by imaging an object, analyze the medical image to determine whether an abnormality is present in the medical image, if an abnormality is present in the medical image, generate at least one assistance image and control the display to display both the medical image and the at least one assistance image, and if an abnormality is not present in the medical image, control the display to display only the medical image, and not the at least one assistance image.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 4 is a flowchart of a medical image transmitting method according to an embodiment;

FIG. 5C is a flowchart of a medical image transmitting method according to another embodiment;

DETAILED DESCRIPTION

Figure 1:
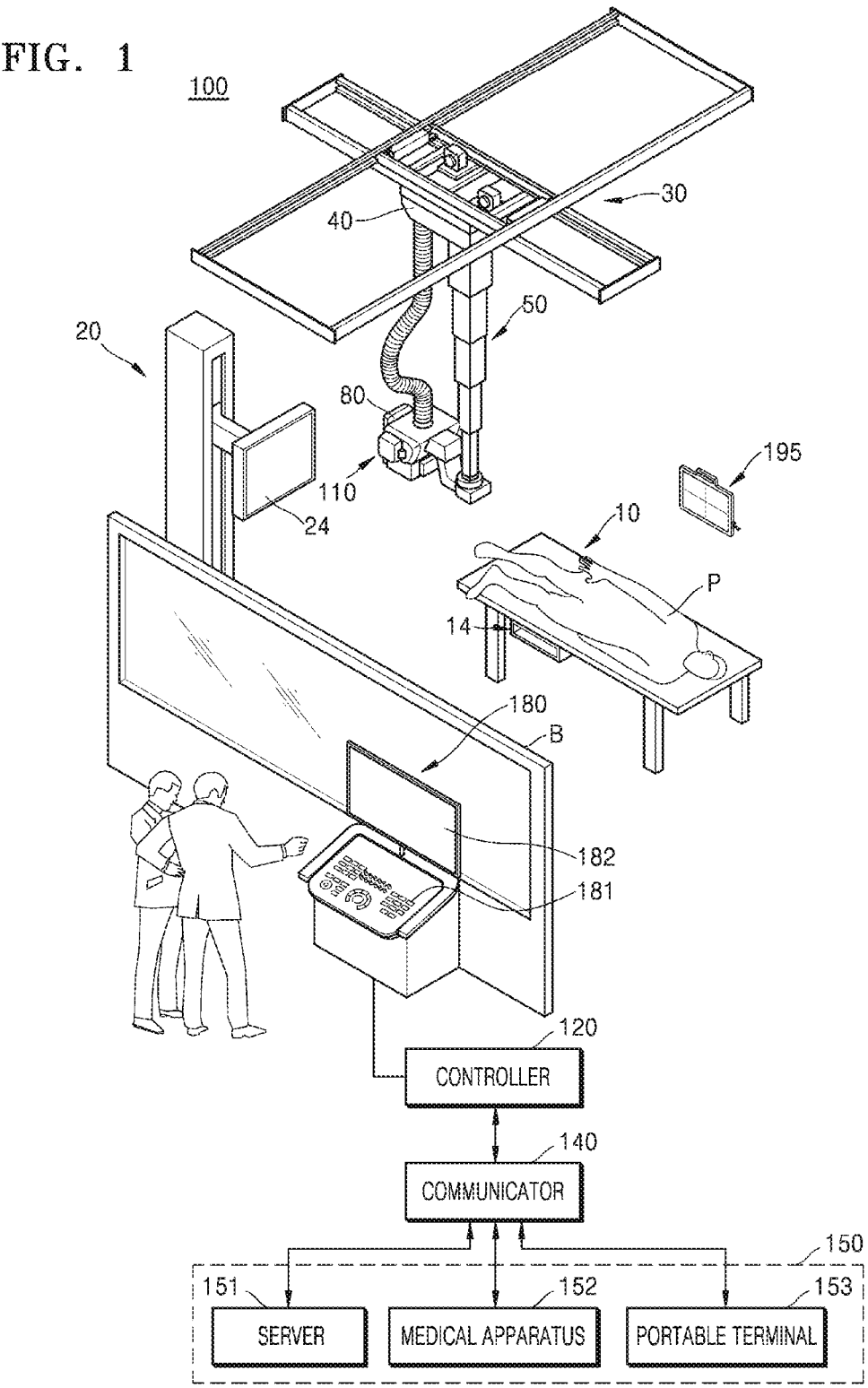
FIG. 1 is an external view and block diagram of a configuration of an X-ray apparatus according to an embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Terms such as "part" and "portion" used herein denote those that may be embodied by software or hardware. According to exemplary embodiments, a plurality of parts or portions may be embodied by a single unit or element, or a single part or portion may include a plurality of elements.

In the present specification, an image may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and may include a human, an animal, or a part of a human or animal. For example, the object may include a body part (an organ, tissue, etc.) or a phantom.

FIG. 1 is an external view and block diagram of a configuration of an X-ray apparatus 100 according to an embodiment.

In FIG. 1, it is assumed that the X-ray apparatus 100 is a fixed X-ray apparatus.

Referring to FIG. 1, the X-ray apparatus 100 includes an X-ray radiation device for generating and emitting X-rays, an X-ray detector 195 for detecting X-rays that are emitted by the X-ray radiation device 110 and transmitted through an object P, and a workstation 180 for receiving a command from a user and providing information to the user.

The X-ray apparatus 100 may further include a controller 120 for controlling the X-ray apparatus 100 according to the received command, and a communicator 140 for communicating with an external device.

All or some components of the controller 120 and the communicator 140 may be included in the workstation 180 or be separate from the workstation 180.

The X-ray radiation device 110 may include an X-ray source for generating X-rays and a collimator for adjusting a region irradiated with the X-rays generated by the X-ray source.

A guide rail 30 may be provided on a ceiling of an examination room in which the X-ray apparatus 100 is located, and the X-ray radiation device 110 may be coupled to a moving carriage 40 that is movable along the guide rail 30 such that the X-ray radiation device 110 may be moved to a position corresponding to the object P. The moving carriage 40 and the X-ray radiation device 110 may be connected to each other via a foldable post frame 50 such that a height of the X-ray radiation device 110 may be adjusted.

The workstation 180 may include an input device 181 for receiving a user command and a display 182 for displaying information.

The input device 181 may receive commands for controlling imaging protocols, imaging conditions, imaging timing, and locations of the X-ray radiation device 110.

The input device 181 may include a keyboard, a mouse, a touch screen, a microphone, a voice recognizer, etc., or a combination of at least two of these components.

The display 182 may be an LCD or OLED display, and may display a screen for guiding a user's input, an X-ray image, a screen for displaying a state of the X-ray apparatus 100, and the like.

The controller 120 may control imaging conditions and imaging timing of the X-ray radiation device 110 according to a command input by the user and may generate a medical image based on image data received from an X-ray detector 195.

Furthermore, the controller 120 may control a position or orientation of the X-ray radiation device 110 or mounting units 14 and 24, each having the X-ray detector 195 mounted therein, according to imaging protocols and a position of the object P. That is, the mounting units 14 and 24 are both able to receive and hold the X-ray detector 195.

The controller 120 may include a memory configured to store programs for performing the operations of the X-ray apparatus 100 and a processor or a microprocessor configured to execute the stored programs. The memory may be RAM or ROM. The memory may be a non-transitory storage medium that stores software programs.

The controller 120 may include a single processor or a plurality of processors or microprocessors. When the controller 120 includes the plurality of processors, the plurality of processors may be integrated onto a single chip or be physically separated from one another.

The X-ray apparatus 100 may be connected to external devices such as an external server 151, a medical apparatus 152, and/or a portable terminal 153 (e.g., a smart phone, a tablet PC, or a wearable electronic device) in order to transmit or receive data via the communicator 140.

The communicator 140 may include at least one component that enables communication with an external device. For example, the communicator 140 may include at least one of a local area communication module, a wired communication module, and a wireless communication module. The communicator may include communication circuitry such as Wi-Fi circuitry, Bluetooth circuitry, or millimeter wave band circuitry.

The communicator 140 may receive a control signal from an external device and transmit the received control signal to the controller 120 so that the controller 120 may control the X-ray apparatus 100 according to the received control signal.

In addition, by transmitting a control signal to an external device via the communicator 140, the controller 120 may control the external device according to the control signal.

For example, the external device may process data of the external device according to the control signal received from the controller 120 via the communicator 140.

The communicator 140 may further include an internal communication module that enables communications between components of the X-ray apparatus 100.

A program for controlling the X-ray apparatus 100 may be installed on the external device and may include instructions for performing some or all of the operations of the controller 120.

The program may be preinstalled on the portable terminal 153, or a user of the portable terminal 153 may download the program from a server providing an application for installation.

The server that provides applications may include a recording medium where the program is stored.

Furthermore, the X-ray detector 195 may be implemented as a fixed X-ray detector that is fixedly mounted to a stand 20 or a table 10 or as a portable X-ray detector that may be detachably mounted in the mounting unit 14 or 24 or can be used at arbitrary positions.

The portable X-ray detector may be implemented as a wired or wireless detector according to a data transmission technique and a power supply method.

The X-ray detector 195 may or may not be a component of the X-ray apparatus 100.

If the X-ray detector 195 is not a component of the X-ray apparatus 100, the X-ray detector 195 may be registered by the user to operate with the X-ray apparatus 100.

Furthermore, in both cases, the X-ray detector 195 may be connected to the controller 120 via the communicator 140 to receive a control signal from or transmit image data to the controller 120.

A sub-user interface 80 that provides information to a user and receives a command from the user may be provided on one side of the X-ray radiation device 110. The sub-user interface 80 may also perform some or all of the functions performed by the input device 181 and the display 182 of the workstation 180. That is, the sub-user interface may include a separate display and a separate input device.

When all or some components of the controller 120 and the communicator 140 are separate from the workstation 180, they may be included in the sub-user interface 80 provided on the X-ray radiation device 110.

Although FIG. 1 shows a fixed X-ray apparatus connected to the ceiling of the examination room, examples of the X-ray apparatus 100 may include other configurations such as a C-arm type X-ray apparatus, a mobile X-ray apparatus, and other X-ray apparatuses having various structures.

With recent developments in image processing technology, such as a computer aided detection (CAD) system and machine learning, medical imaging apparatuses may analyze an obtained medical image by using a computer, and thus detect an abnormal region, which is an abnormal part of an object, and generate a result of the analysis. An image generated again by analyzing the obtained medical image as described above is referred to as an 'assistance image' or 'read assistance image'. When the assistance image is provided to a doctor, the doctor may more easily diagnose whether an abnormality is present in an object, by referring to the assistance image.

Medical imaging apparatuses may transmit a medical image and at least one assistance image to an external apparatus. Accordingly, the external apparatus may also diagnose a patient by using the medical image and the assistance image.

However, when a medical image and at least one assistance image are provided to an external apparatus, a memory capacity, a data processing amount, and a data transmission amount, which are required, relatively increase, compared to when the medical image is transmitted to the external apparatus. Hereinafter, an image generated again by analyzing the obtained medical image will be referred to as a read assistance image.

To improve the ease of reading of a medical image or a diagnosis using a medical image, a medical imaging apparatus or an external apparatus (for example, an external apparatus 150) that receives a medical image from the medical imaging apparatus may generate a read assistance image by using the medical image and may provide the generated read assistance image to a user.

In detail, the medical imaging apparatus may analyze an obtained medical image by using a computer, according to image processing technology, such as a computer aided detection (CAD) system or machine learning. The medical imaging apparatus may detect an abnormal region, which is an abnormal part of an object, or may generate a result of the analysis.

In general, the medical imaging apparatus that generates a read assistance image and provides the generated read assistance image to a user may be the controller 120 of the X-ray apparatus 100 of FIG. 1, the workstation 180 of the X-ray apparatus 100, a picture archiving communications system (PACS) server, a PACS viewer, or the like. The medical imaging apparatus may also be any electronic device capable of obtaining a medical image and generating a read assistance image based on the obtained medical image.

Medical imaging apparatuses obtain medical images, analyze each of the obtained medical images, and generate one or more read assistance images associated with each of the obtained medical images. The medical imaging apparatuses may transmit the obtained medical images and the read assistance images to an external apparatus such that the external apparatus may use the received medical images and the received read assistance images.

For example, when the medical imaging apparatus is the X-ray apparatus 100 of FIG. 1, a space where a doctor diagnoses whether an object has an abnormality by using a medical image and read assistance images is usually separated from a space where the X-ray apparatus 100 is mounted. For example, the X-ray apparatus 100 may be located in a radiation room, and reading by a doctor may be performed in a doctor's office separate from the radiation room. In this case, the X-ray apparatus 100 needs to transmit an obtained medical image and an obtained read assistance image to an external apparatus, for example, a PACS viewer or a doctor's computer provided in the doctor's office. Then, the doctor may view the medical image and the read assistance image via the PACS viewer and may diagnose the object or patient.

As another example, when the medical imaging apparatus is the X-ray apparatus 100 of FIG. 1, a medical image and read assistance images obtained by the X-ray apparatus 100 need to be stored in a server, for example, a PACS server, or an electronic device, in order to store medical recordings of a patient. In this case, the X-ray apparatus 100 needs to transmit the obtained medical image and the obtained read assistance images to the server or the electronic device physically distinguished from the X-ray apparatus 100.

However, when an object has no abnormalities, a doctor, for example, may easily determine that the object has no abnormalities, by only using the obtained medical image. In other words, without using the read assistance image, a user, such as a doctor, may easily ascertain that the object has no abnormalities, by only using the original medical image. Accordingly, when an object has no abnormalities, it is not necessary to generate a read assistance image and transmit and/or store the generated read assistance image to and/or in an external apparatus, for example, a PACS viewer.

To generate a read assistance image and transmit the generated read assistance image to the external apparatus, a data processing amount, a memory capacity, and a read assistance image acquisition time period that are required for image processing all increase, and a required data transmission amount also increases. This time increase that occurs as a result of a need to generate and transmit a read assistance image may degrade a workflow of medical image reading and may degrade reading efficiency.

In a medical imaging apparatus according to an embodiment and a medical image transmitting method performed thereby, a medical image may be primarily analyzed to determine whether an object has an abnormality, and it may be automatically determined, based on the primary determination, whether to transmit a read assistance image to an external apparatus. Accordingly, unnecessary generation and/or transmission of the read assistance image may be prevented. That is, by determining whether or not to generate or transmit a read assistance image, the medical imaging apparatus can process medical image data more efficiently because computational resources that would otherwise be used for an unnecessary process (i.e., generating a read assistance image when there is no abnormality) can be preserved and used for other more productive computational objectives. This permits the medical imaging apparatus to process data more quickly, and/or at lower cost. Furthermore, memory requirements and data transmission requirements are reduced when this process is not performed. In short, computational efficiency in several respects is enhanced. A medical imaging apparatus according to an embodiment capable of optimizing a workflow of medical image reading and increasing the reading efficiency of a doctor, and a medical image transmitting method performed thereby will now be described in detail with reference to the accompanying drawings.

Figure 2:
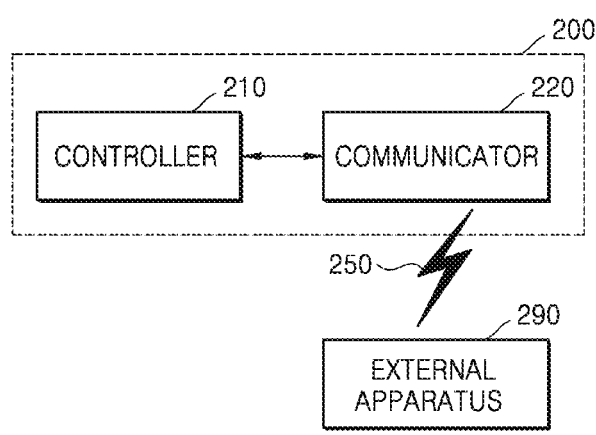
FIG. 2 is a block diagram of a medical imaging apparatus according to an embodiment.

FIG. 2 is a block diagram of a medical imaging apparatus 200 according to an embodiment.

The medical imaging apparatus 200 according to an embodiment may include any electronic device capable of obtaining a medical image and analyzing the obtained medical image to generate a read assistance image.

In detail, a medical imaging apparatus may autonomously obtain a medical image via medical image capturing or may receive a medical image obtained by another medical imaging apparatus.

For example, the medical imaging apparatus 200 according to an embodiment may be the X-ray apparatus 100 of FIG. 1. In this case, the X-ray apparatus 100 may autonomously obtain an X-ray image, which is a medical image, via X-ray scanning. In detail, the medical imaging apparatus according to an embodiment may be included in the controller 120 or the workstation 180 of the X-ray apparatus 100 of FIG. 1.

As another example, the medical imaging apparatus 200 may be the server 151, the medical apparatus 152, or the portable terminal 153 connected to a medical imaging apparatus, such as the X-ray apparatus 100 of FIG. 1, via a wired connection or a wireless communication network. In this case, the medical apparatus 152 may receive the X-ray image obtained by the X-ray apparatus 100 as a medical image, and may analyze the received medical image to generate a read assistance image.

A medical image obtained and used by a medical image transmitting method according to an embodiment and a medical imaging apparatus performing the medical image transmitting method may be any image that enables a determination as to whether an object has an abnormality. In detail, the medical image may be an image of an object obtained by at least one of the X-ray apparatus 100 performing X-ray scanning, a CT system, an MRI system, an ultrasound diagnosis apparatus, and another medical imaging system.

The object may include a body part of a person, for example, a patient, who is a diagnosis target, and may include an organ (e.g., the liver, the heart, the womb, the brain, a breast, or the abdomen), or a blood vessel, or plural blood vessels.

Throughout the specification, a "user" may be, but is not limited thereto, a medical provider, such as a doctor, a nurse, a health care technician, or a medical imaging expert, or may be an engineer who manages medical appliances.

A case where a medical image obtained and used by a medical image transmitting method according to an embodiment and a medical imaging apparatus performing the medical image transmitting method is an X-ray image will now be illustrated and described.

A case where the medical imaging apparatus 200 according to an embodiment is the X-ray apparatus 100 of FIG. 1 will now be illustrated and described.

Referring to FIG. 2, the medical imaging apparatus 200 includes a controller 210 and a communicator 220. When the medical imaging apparatus 200 corresponds to the X-ray apparatus 100 of FIG. 1, the controller 210 and the communicator 220 included in the medical imaging apparatus 200 may respectively correspond to either the controller 120 or workstation 180 and the communicator 140 of the X-ray apparatus 100. Thus, a redundant description thereof will be omitted.

The controller 210 obtains a medical image obtained by imaging an object. The controller 210 may first determine whether the object has an abnormality, by analyzing the received medical image, and secondly determine whether to transmit at least one read assistance image associated with the medical image, based on the first determination. When the object has no abnormalities, the controller 210 controls the medical image to be transmitted to an external apparatus 290. In detail, when the object has no abnormalities, the controller 210 controls the medical image, except for the read assistance image, to be transmitted to an external apparatus 290. In response to the medical image, the controller 210 may automatically perform the above-described two determinations. For convenience of explanation, the determination as to whether an object has an abnormality will now be referred to as a first determination, and the determination as to whether to transmit at least one read assistance image will now be referred to as a second determination.

The controller 210 may include a memory (not shown), for example, ROM or RAM, and at least one processor (not shown) that performs instructions for performing the above-described operations. The at least one processor included in the controller 210 may operate to execute the instructions for performing the above-described operations. In detail, the at least one processor included in the controller 210 may operate to execute a program including the instructions for performing the above-described operations.

A case where an object has an abnormality may be referred to as a case where the object has any shape other than the shape of a healthy tissue or a case where the object is in a state other than a healthy state. For example, the case where the object has an abnormality may be a case where a certain part of the object has a disease.

A read assistance image is generated by processing a medical image obtained via medical image capturing, and may be an image obtained by processing the medical image in order to facilitate reading of the object. The read assistance image may include an image processed such that a disease may be easily detected.

In detail, the read assistance image may be an image on which an abnormal part is automatically detected and displayed, or an image on which the type of disease generated on the abnormal part, a result of analyzing a disease or a disease candidate, or probability information about what the generated disease is.

For example, when the original medical image is a chest X-ray image, the read assistance image may include a bone suppression image on which an organ existing in the chest is more clearly shown by removing bones existing in the chest, a lesion-detected CAD image on which a lesion existing in the object is detected via CAD and displayed, and an abnormality map on which an abnormal portion of a tissue or detailed areas included in the object is detected and displayed. The read assistance image may further include any image obtained by processing the original medical image in order to help determine whether the object has an abnormality. In the above example, with regard to the bone suppression image, when a lesion is located in a soft tissue included in the object, for example, a lung, it is difficult to observe a lung part hidden by bones from the original medical image. However, when the bones are removed from the chest X-ray image, the lung may be more clearly observed, and thus the lesion located in the lung may be easily read.

The read assistance image may be represented as data having no image shapes. In detail, the read assistance image may include analysis data indicating that the object has an abnormality.

For example, the read assistance image may include, as information obtained based on the bone suppression image, information representing a generation location of a disease, a revelation shape of the disease, the risk of the disease, the accuracy of detection of the disease, and a reliability when an abnormality is determined as a disease, which is information indicating whether the object has an abnormality. The disease refers to all cases where the object has an abnormality, and thus may include a pneumothorax, a lesion, a tumor, a tissue change, and an abnormal organ shape generated within the object. The object having an abnormality may include not only a case where the object has a disease, but also a case where a lesion is present in the object (for example, deformation or the like of a cell, a tissue, an organ, or the like before a tumor is generated). The read assistance image may include an image of the lesion and a marking indicating the presence of the lesion.

The controller 210 may perform the above-described operation of determining whether an object has an abnormality and an abnormal portion analyzing operation via machine learning, and this will be described in detail with reference to FIGS. 3 and 7.

The communicator 220 transmits the medical image to the external apparatus 290 under the control of the controller 210.

The communicator 220 may include one or more components that enable communication with the external apparatus 290. For example, the communicator 220 may include a short distance communication module, a wired communication module, and a wireless communication module.

In detail, the communicator 220 may be connected to a wired/wireless network 250 and thus may perform communication with the external apparatus 290, for example, an external apparatus such as the server 151, the medical apparatus 152, or the portable terminal 153 of FIG. 1.

The external apparatus 290 may be an electronic apparatus capable of receiving a medical image and at least one read assistance image and performing at least one operation from among storing, processing, analyzing, and displaying the received images.

In detail, the external apparatus 290 may be a PACS (not shown), for example, a PACS server or a PACS viewer. Accordingly, the medical imaging apparatus 200 may exchange data with a hospital server or another medical apparatus in a hospital, which is connected to the medical imaging apparatus 200 via a PACS (not shown) connected via the communicator 220.

In detail, when it is determined, based on the medical image, that the object has no abnormalities, the controller 210 may control the medical image to be transmitted to the external apparatus 290, without generating a read assistance image associated with the medical image.

A detailed structure and a detailed operation of the medical imaging apparatus 200 will now be described in detail with reference to FIGS. 3 through 8D.

Figure 3:
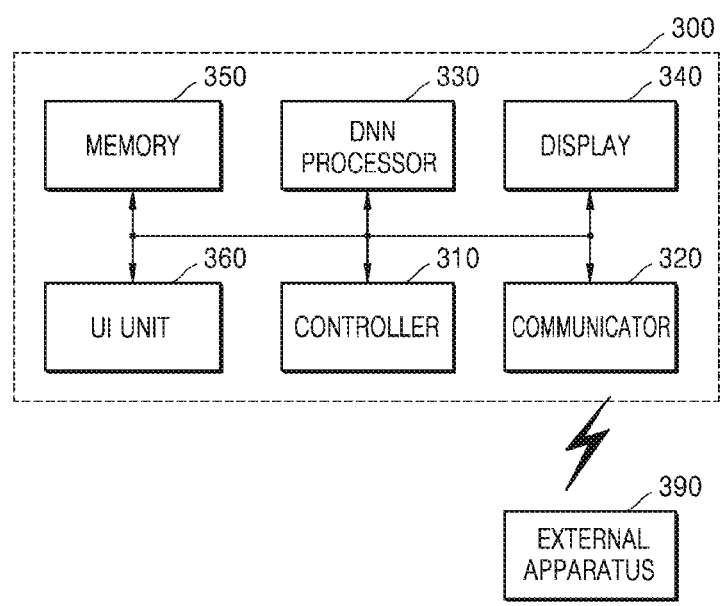
FIG. 3 is a block diagram of a medical imaging apparatus according to another embodiment.

FIG. 3 is a block diagram of a medical imaging apparatus 300 according to another embodiment. A controller 310 and a communicator 320 included in the medical imaging apparatus 300 of FIG. 3 may respectively correspond to the controller 210 and the communicator 220 of the medical imaging apparatus 200 of FIG. 2. An external apparatus 390 of FIG. 3 may correspond to the external apparatus 290 of FIG. 2. Accordingly, descriptions of the medical imaging apparatus 300 that are the same as those made with reference to FIG. 2 are not repeated herein.

Referring to FIG. 3, the medical imaging apparatus 300 may further include at least one of a deep neural network (DNN) processor 330, a display 340, a memory 350, and a user interface (UI) unit 360, compared with the medical imaging apparatus 200 of FIG. 2.

The controller 310 obtains a medical image obtained by imaging an object. The controller 310 may determine whether the object has an abnormality, by analyzing the received medical image, and determine whether to transmit at least one read assistance image associated with the medical image, based on the determination.

The medical imaging apparatus 300 may obtain a medical image according to various methods. In detail, the medical imaging apparatus 300 may include an image capturing apparatus (not shown), and the controller 310 may drive the image capturing apparatus to obtain a medical image. For example, when the medical imaging apparatus 300 corresponds to the X-ray apparatus 100 of FIG. 1, the controller 310 may drive the X-ray radiation device 110 and the X-ray detector 195 to obtain an X-ray image, which is the medical image.

The medical imaging apparatus 300 may receive the medical image from an external source. In detail, when the medical imaging apparatus 300 is implemented as an apparatus independent from an electronic apparatus that performs medical image capturing, for example, the X-ray apparatus 100 of FIG. 1, the medical imaging apparatus 300 may receive the medical image from the electronic apparatus performing medical image capturing (hereinafter, referred to as an external medical imaging apparatus) via a wired/wireless communication network. In this case, the medical imaging apparatus 300 may receive the medical image from the external medical imaging apparatus via the communicator 320. In detail, the medical imaging apparatus 300 may receive an X-ray image, which is a medical image, from the X-ray apparatus 100 of FIG. 1 or the like via the communicator 320, and may transmit the received X-ray image to the controller 310.

In detail, when it is determined based on the medical image that the object has no abnormalities, the controller 310 may control the medical image except for a read assistance image associated with the medical image to be transmitted to the external apparatus 390. On the other hand, when it is determined based on the medical image that the object has an abnormality, the controller 310 may control both the medical image and the read assistance image associated with the medical image to be transmitted to the external apparatus 390.

The read assistance image may be generated according to a result of a determination made by the medical imaging apparatus 300 as to whether the object has an abnormality. In detail, when the medical imaging apparatus 300 determines that the object has an abnormality, the medical imaging apparatus 300 may generate a read assistance image, and, when the medical imaging apparatus 300 determines that the object has no abnormalities, the medical imaging apparatus 300 may generate no read assistance images.

Alternatively, the medical imaging apparatus 300 may obtain a read assistance image, regardless of a result of the determination as to whether the object has an abnormality. In detail, the read assistance image may be previously obtained before the medical imaging apparatus 300 determines whether the object has an abnormality.

In detail, when it is determined based on the medical image that the object has no abnormalities, the controller 310 may not generate a read assistance image associated with the medical image and may control the medical image to be transmitted to the external apparatus 390. When the medical image is obtained, the controller 310 may automatically perform the above-described determining operation and the above-described transmitting operation.

On the other hand, when it is determined based on the medical image that the object has an abnormality, the controller 310 may generate at least one read assistance image associated with the medical image and may control the medical image and the at least one read assistance image to be transmitted to the external apparatus 390.

As another example, the controller 310 may obtain a medical image and at least one read assistance image, and, when it is determined based on the medical image that the object has no abnormalities, the controller 310 may control the medical image except for the at least one read assistance image to be transmitted to the external apparatus 390. The controller 310 may obtain the medical image and the at least one read assistance image, and, when it is determined based on the medical image that the object has an abnormality, the controller 310 may control both the medical image and the at least one read assistance image to be transmitted to the external apparatus 390.

The determination made based on the medical image by the controller 310 as to whether the object has an abnormality may be performed via mechanical learning. In detail, mechanical learning may be performed via a CAD operation of determining and detecting whether an object has an abnormality via a computer operation, via statistical learning based on data, or via an artificial intelligence (AI) system that performs mechanical learning according to AI technology.

The AI system is a computer system that implements human-level intelligence, and becomes increasingly smarter while autonomously performing learning and determination, in contrast with existing rule-based smart systems. Because AI systems increase a recognition rate and more accurately understand user's preferences the more they are used, existing rule-based smart systems are being gradually replaced by deep-learning AI systems.

AI technology includes mechanical learning (deep learning) and element technologies employing the mechanical learning.

The mechanical learning is an algorithm technology that classifies/learns the features of pieces of input data by itself, and each of the element technologies is a technology using a mechanical learning algorithm, such as deep learning, and includes technical fields, such as linguistic understanding, visual understanding, inferring/prediction, a knowledge expression, and operation control.

The controller 310 according to an embodiment may use learning technology included in AI technology for inferring and/or prediction, when determining whether the object has an abnormality. In detail, learning technology for inferring and/or prediction is a technology for logically inferring results based on input information and outputting results corresponding to the input information, and includes knowledge/probability-based inferring, optimization prediction, a preference-based plan, recommendation, and the like. For example, AI technology may analyze an object included in a received medical image, infer or predict whether the object has an abnormality, and output a result of the inferring or prediction.

In detail, inferring and prediction according to AI technology may be performed via an operation based on a neural network. In detail, an operation based on a neural network, such as a DNN, may be used. The DNN operation may include a convolution neural network (CNN) operation and the like.

In detail, a data recognition model may be implemented via the above-illustrated neural network, and may be learned using learning data. Data input using a learned data recognition model, for example, a medical image, may be analyzed or classified, and thus what abnormality has occurred in an object image may be analyzed and classified from the medical image.

For example, the medical imaging apparatus 300 according to an embodiment may determine whether the object has an abnormality, via learning and inferring operations based on a DNN. In detail, the medical imaging apparatus 300 may determine whether the object has an abnormality, via learning and inferring operations based on a CNN operation, which is a sort of a DNN operation.

At least one processor that performs learning and inferring operations based on a DNN may be referred to as a DNN processor. The DNN processor may be manufactured in the form of a dedicated hardware chip for AI, or may be manufactured as a portion of an existing general-use processor (for example, a central processing unit (CPU) or an application processor) or a graphics dedicated processor (for example, a graphics processing unit (GPU)) or a portion of the controller 310 and may be mounted on the above-described various electronic devices. When the controller 310 includes a DNN processor, the controller 310 may include at least one processor that performs the aforementioned operations, and one of the at least one processor may be used as the DNN processor.

In detail, the controller 310 may determine whether the object has an abnormality, via learning and inferring operations based on a DNN. In detail, the controller 310 may include a DNN processor, and the DNN processor may be implemented using a special chip, processor, or module.

The medical imaging apparatus 300 may include the DNN processor 330, separate from the controller 310.

The DNN processor 330 may determine whether the object has an abnormality, via learning and inferring operations based on a DNN. The DNN processor 330 may transmit a result of the determination to the controller 310. In this case, the controller 310 may ascertain whether the object has an abnormality, based on a determination result obtained by the DNN processor 330.

The above-described learning and inferring operations based on a DNN will be described in more detail later with reference to FIG. 7.

The display 340 may display a UI screen, user information, image processing information, and the like. In detail, the display 340 may display a UI screen generated under the control of the controller 310. The UI screen may include at least one of a medical image and at least one read assistance image. The UI screen may include information about whether the object has an abnormality, which is obtained by analyzing the medical image. For example, the display 340 may correspond to the display 182 included in the X-ray apparatus 100 of FIG. 1. The UI screen displayed on the display 340 will be described in more detail with reference to FIGS. 9 through 12B.

The memory 350 may include at least one program necessary for the medical imaging apparatus 300 to operate, or at least one instruction necessary for the at least one program to be executed. The memory 350 may also include one or more processors for performing the above-described operations. The memory 350 may be a non-transitory storage in some embodiments.

The memory 350 may store at least one of the medical image and the at least one read assistance image, and may store information about whether the object has an abnormality.

The UI unit 360 may receive certain data or a certain command from a user. The UI unit 360 may correspond to at least one of the sub-user interface 80 and the input device 181 of FIG. 1. The UI unit 360 may be implemented using a touch screen integrally formed with the display 340. As another example, the UI unit 360 may include a user input device, such as a pointer, a mouse, or a keyboard.

According to an embodiment, the controller 310 may provide information including a result of the first determination as to whether the object has an abnormality, to a user of at least one of the medical imaging apparatus 300 and the external apparatus 390.

According to an embodiment, the controller 310 may receive a signal corresponding to a user input, and may perform the second determination as to whether to transmit at least one read assistance image, based on the received signal corresponding to the user input.

In detail, the controller 310 may control the display 340 to display a UI screen including a result of the first determination. The controller 310 may also control the medical imaging apparatus 300 to output an audio signal including the result of the first determination via a speaker (not shown) included inside or outside the medical imaging apparatus 300.

The controller 310 may also control information including the result of the first determination to be transmitted to the external apparatus 390. Accordingly, the user of the external apparatus 390 may recognize the result of the first determination.

Then, the user of at least one of the medical imaging apparatus 300 and the external apparatus 390 may recognize the result of the first determination and may determine whether to transmit the medical image to the external apparatus 390 or whether to transmit both the medical image and the at least one read assistance image to the external apparatus 390. In detail, based on the result of the first determination, the user may input, via the UI unit 360 of the medical imaging apparatus 300, a user input indicating whether to transmit the medical image to the external apparatus 390 or whether to transmit both the medical image and the at least one read assistance image to the external apparatus 390.

Alternatively, based on the result of the first determination, the user may input, to the external apparatus 390, the user input indicating whether to transmit the medical image to the external apparatus 390 or whether to transmit both the medical image and the at least one read assistance image to the external apparatus 390. When the external apparatus 390 receives the aforementioned user input, the external apparatus 390 may transmit a signal corresponding to the user input to the medical imaging apparatus 300. Accordingly, the medical imaging apparatus 300 may determine whether to transmit the at least one read assistance image to the external apparatus 390, based on the received signal corresponding to the user input.

As described above, the controller 310 of the medical imaging apparatus 300 may perform the second determination as to whether to transmit the at least one read assistance image, based on the user input or the signal corresponding to the user input. In detail, when the user input is an input requesting the at least one read assistance image to be not transmitted to the external apparatus 390, the controller 310 may control the medical image except for the at least one read assistance image to be transmitted to the external apparatus 390, according to the user input. On the other hand, when the user input is an input requesting the at least one read assistance image to be transmitted to the external apparatus 390, the controller 310 may control the at least one read assistance image together with the medical image to be transmitted to the external apparatus 390, according to the user input.

FIG. 4 is a flowchart of a medical image transmitting method 400 according to an embodiment. The medical image transmitting method 400 according to an embodiment may be performed by the medical imaging apparatus 200 or 300. Accordingly, operations of the medical image transmitting method 400 may be performed by components of the medical imaging apparatus 200 or 300, respectively, and the medical image transmitting method 400 may include the same structural features as the medical imaging apparatus 200 or 300. Accordingly, descriptions of the medical image transmitting method 400 that are the same as those made with reference to FIGS. 1 through 3 are not repeated herein.

The medical image transmitting method 400 will now be described in detail with reference to the medical imaging apparatus 300 of FIG. 3.

Referring to FIG. 4, in the medical image transmitting method 400 according to an embodiment, a medical image of an object is obtained, in operation S410. Operation S410 may be performed under the control of the controller 310.

In the case that the medical image transmitting method 400 is performed by the medical imaging apparatus 300, the medical imaging apparatus 300 may include an image capturing apparatus (not shown), and the controller 310 may drive the image capturing apparatus to obtain a medical image.

For example, the controller 310 may drive the X-ray radiation device 110 and the X-ray detector 195 to obtain an X-ray image, which is the medical image. Alternatively, the medical imaging apparatus 300 may receive a medical image from an external source. In this case, the medical imaging apparatus 300 may receive the medical image from an external medical imaging apparatus via the communicator 320.

In operation S420, it is determined whether the object has an abnormality, based on the medical image received in operation S410, and it is determined, based on the determination, whether to transmit at least one read assistance image associated with the medical image. When the medical image is received in operation S410, operation S420 may be automatically performed by the controller 310. Alternatively, when the DNN processor 330 determines whether the object has an abnormality, operation S420 may be performed by the controller 310, based on a determination result obtained by the DNN processor 330.

Also, in operation S420, the second determination as to whether to transmit the at least one read assistance image may be performed based on a user input (or a signal corresponding to the user input). The user input serving as a basis for determining whether to transmit the at least one read assistance image has been described above with reference to FIG. 3, and thus a detailed description thereof will be omitted.

When it is determined in operation S420 that the object has no abnormalities, the medical image may be transmitted to an external apparatus, in operation S430. In detail, when it is determined in operation S420 that the object has no abnormalities, the medical image except for the read assistance image may be transmitted to an external apparatus, in operation S430. Operation S430 may be performed by the communicator 320 under the control of the controller 310.

Figure 5A:
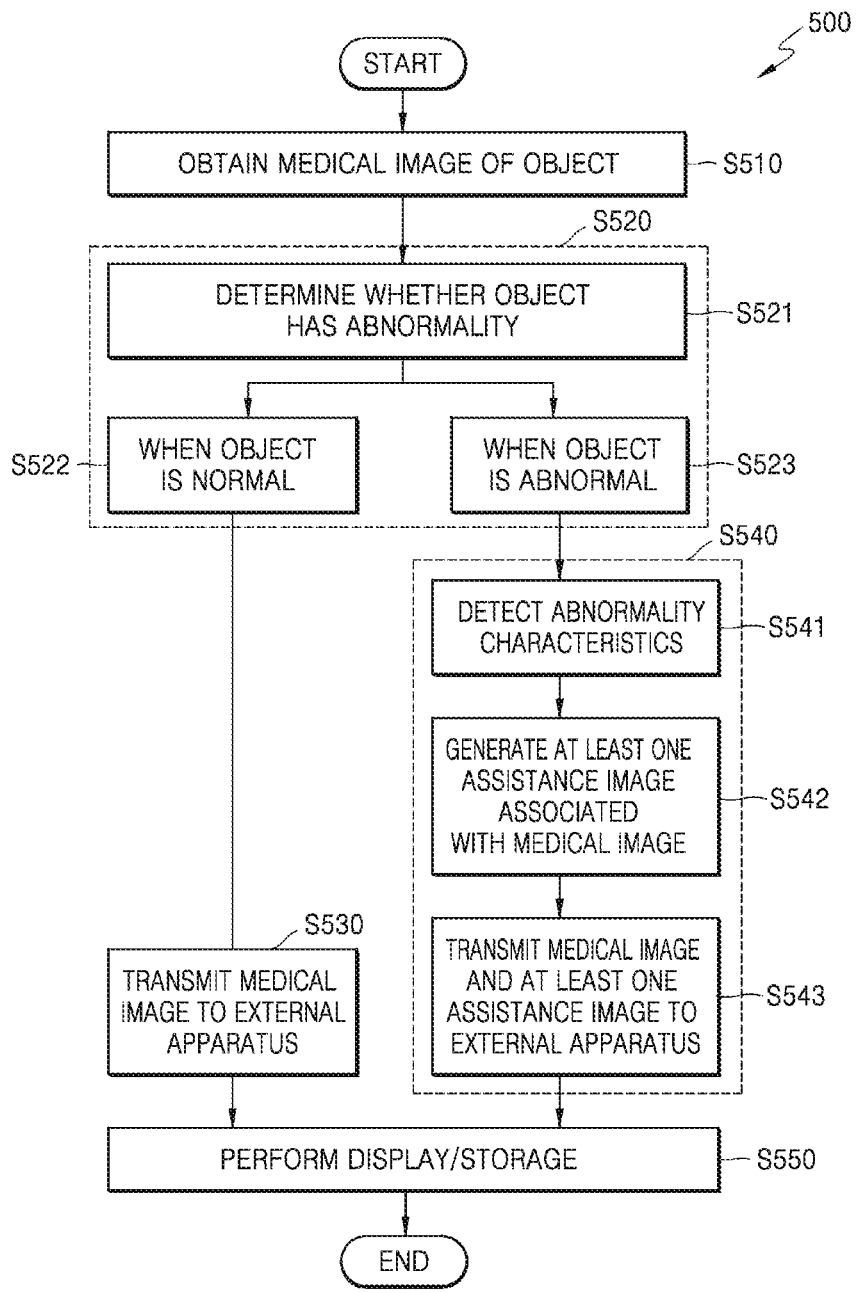
FIG. 5A is a flowchart of a medical image transmitting method according to another embodiment.

FIG. 5A is a flowchart of a medical image transmitting method 500 according to another embodiment. Operations S510, S520 and S530 of the medical image transmitting method 500 of FIG. 5A may correspond to operations S410, S420 and S430 of the medical image transmitting method 400 of FIG. 4, respectively.

Referring to FIG. 5A, in the medical image transmitting method 500, a medical image of an object is obtained, in operation S510.

Figure 6:
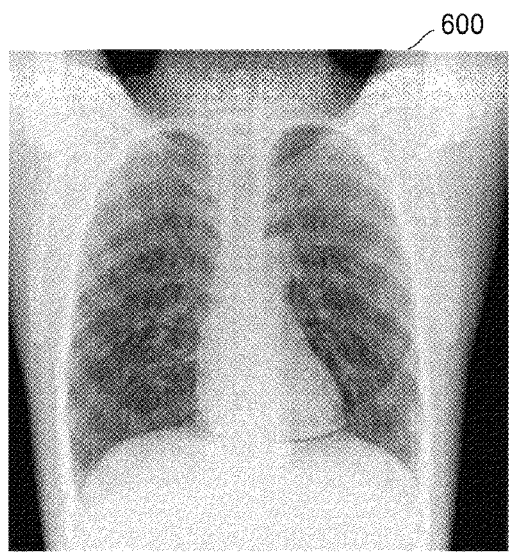
FIG. 6 illustrates a medical image obtained by an apparatus and a method, according to an embodiment.

FIG. 6 illustrates a medical image obtained by an apparatus and a method according to an embodiment.

The medical image received in operation S510 may be, for example, an X-ray image. Referring to FIG. 6, the medical image received in operation S510 may be an X-ray image 600 obtained via X-ray scanning. The medical image received in operation S510 may be an original image obtained via X-ray scanning. Alternatively, the X-ray image 600 may be a post-processed image obtained by post-processing the original image. The post-processing may include, for example, processing for reducing or removing noise of the original image, and filter processing for clarifying an image. The medical image received in operation S510 is an image representing the object without changes, and may be an image before processing for generating a read assistance image.

In operation S520, it is determined whether the object has an abnormality, based on the medical image received in operation S510, and it is determined, based on the determination, whether to transmit at least one read assistance image associated with the medical image.

In detail, operation S520 may include operation S521 of determining whether the object has an abnormality and an operation of classifying a result of the determination into a case S522 when the object is normal and a case S523 when the object is abnormal.

Operation S520 may be performed by the controller 310 or the DNN processor 330. As described above, operation S520 may be performed via a CAD operation or an AI system that performs mechanical learning according to AI technology. A case where the determining operation S520 is performed via a DNN operation that is performed according to AI technology will now be illustrated and described. The determining operation S520 via a DNN operation will be described in more detail with reference to FIG. 7. FIG. 7 is a view for explaining a DNN that is used in an apparatus and a method according to an embodiment. A case where an operation via a DNN 720 is performed by the DNN processor 330 will now be illustrated and described.

The DNN processor 330 may perform an operation via the DNN 720, the DNN 720 including an input layer, a hidden layer, and an output layer. The hidden layer may include a plurality of layers, for example, a first hidden layer, a second hidden layer, and a third hidden layer.

Figure 7:
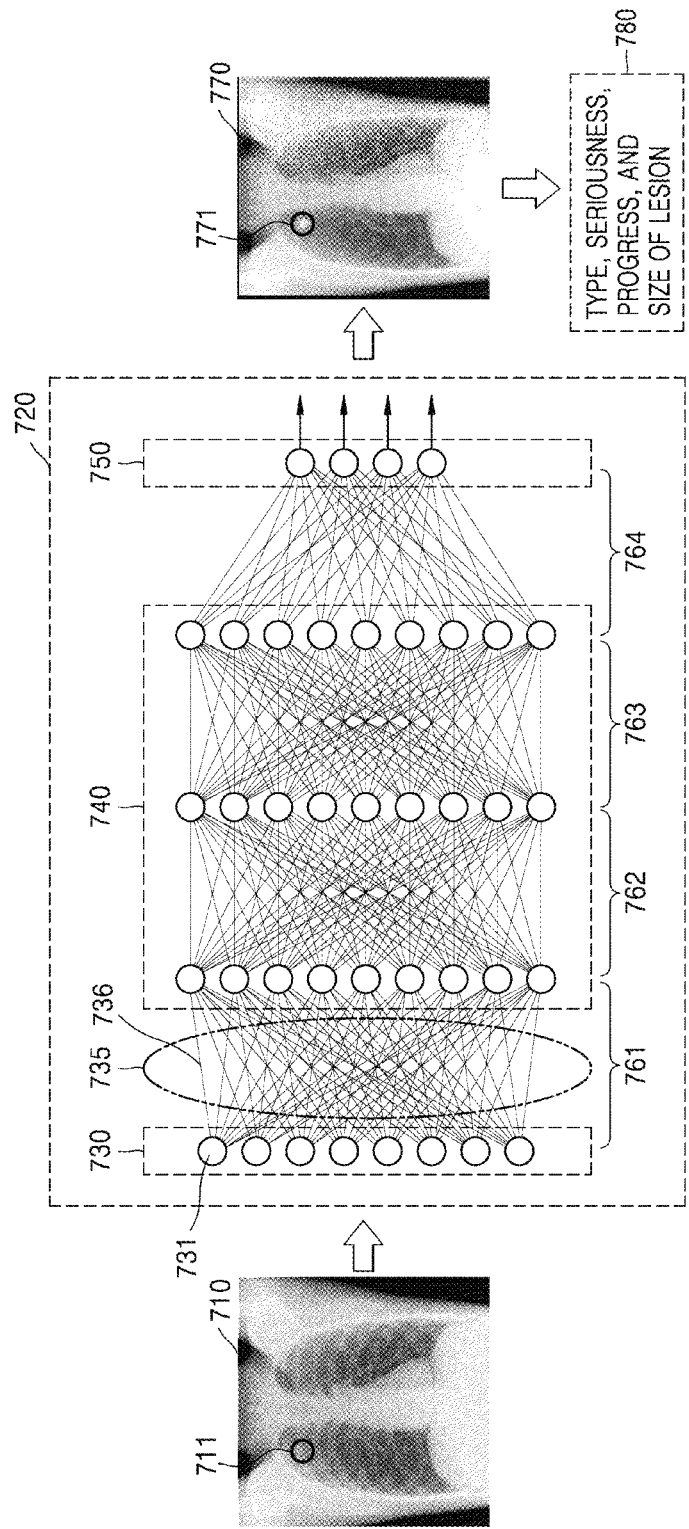
FIG. 7 is a view for explaining a deep neural network (DNN) that is used in an apparatus and a method, according to an embodiment.

Referring to FIG. 7, the DNN 720 includes an input layer 730, a hidden layer 740, and an output layer 750. FIG. 7 illustrates the DNN 720 that performs a DNN operation of analyzing information included in a medical image, which is input data, to determine whether an object image has an abnormality on the medical image, and outputting analysis information about a part of the object having an abnormality. In detail, when the input data is an X-ray image 710, the DNN 720 outputs, as output data, result data obtained by analyzing an object image included in the X-ray image 710. The X-ray image 710 corresponds to the medical image received in operation S510.

The plurality of layers that form the DNN 720 may include a plurality of nodes 731 that receive data. As shown in FIG. 7, two adjacent layers are connected to each other via a plurality of edges 736. Because the nodes have weighted values, respectively, the DNN 720 may obtain output data, based on a value obtained by performing an arithmetic operation, for example, multiplication, with respect to an input signal and each of the weighted values.

The DNN 720 may perform inferring and prediction operations based on a neural network, and the DNN operation may include a CNN operation and the like. In other words, the DNN 720 may be implemented using a CNN that performs a CNN operation.

Referring to FIG. 7, the input layer 730 receives the X-ray image 710 obtained by scanning a chest, which is an object. The X-ray image 710 may be an image obtained by scanning an object having a lesion 711 on his or her right chest.

Referring to FIG. 7, the DNN 720 may include a first layer 761 formed between the input layer 730 and the first hidden layer, a second layer 762 formed between the first hidden layer and the second hidden layer, a third layer 763 formed between the second hidden layer and the third hidden layer, and a fourth layer 764 formed between the third hidden layer and the output layer 750.

The plurality of nodes included in the input layer 730 of the DNN 720 receive a plurality of pieces of data corresponding to the X-ray image 710. The plurality of pieces of data may be a plurality of partial images generated by performing filter processing of splitting the X-ray image 710.

Via operations in the plurality of layers included in the hidden layer 740, the output layer 750 may output pieces of output data/image 770 and 780 corresponding to the X-ray image 710. In the shown illustration, because the DNN 720 performs an operation to obtain data indicating whether the object included in the input X-ray image 710 has an abnormality, the output layer 750 may output an image 770 displaying a lesion 771 detected from the input X-ray image 710 and/or data 780 obtained by analyzing the detected lesion 771. The data 780 is information indicating the characteristics of the detected lesion 771, and may include the type, seriousness, progress, size, and location of the lesion 771.

To increase the accuracy of output data output via the DNN 720, learning may be performed in a direction from the output layer 750 to the input layer 730, and the weighted values may be corrected such that the accuracy of output data increases. Accordingly, before the X-ray image 710 is input, the DNN 720 may perform deep learning by using a plurality of different chest X-ray images to correct the respective weighted values of the nodes in a direction for accurately detecting an abnormal part included in a chest X-ray image, namely, in a direction that increases the accuracy of detecting the abnormal part.

The DNN 720 may automatically perform an operation of determining whether the object is normal or abnormal. The DNN 720 may automatically perform an operation of analyzing an abnormal object to generate an image or data indicating the characteristics of an abnormal part of the abnormal object.

In detail, in operation S520 of FIG. 5A, it may be only determined whether the object has an abnormality. In other words, in operation S520 of FIG. 5A, only an operation of determining whether the object has an abnormality and thus is in an abnormal state or has no abnormalities and is thus in a normal state may be performed via the DNN 720. An additional analysis operation for obtaining the data 780 of FIG. 7 may not be performed in operation S520.

In other words, to perform operation S520, the DNN 720 performs an operation of determining whether the object is normal or abnormal. When it is determined that the object is in an abnormal state, the DNN 720 may perform a learning operation corresponding to operation S540.

Referring back to FIG. 5A, when it is determined in operation S521 that the object is normal (case S522), only the medical image except for the read assistance image is transmitted to an external apparatus, in operation S530. That is, operation S530 involves skipping the image generation operation S542, and the operation S541.

On the other hand, when it is determined in operation S521 that the object is abnormal (case S523), operation S540 may be further performed. Operation S540 may be performed by the controller 310 or the DNN processor 330. In detail, operation S541 may be performed via the DNN 720.

In detail, when it is determined that the object is abnormal (case S523), at least one read assistance image associated with the medical image may be generated, in operation S542.

The medical image transmitting method 500 may further include operation S541 to analyze the medical image when it is determined that the object is abnormal (case S523). Based on a result of the analysis, at least one read assistance image associated with the medical image may be generated, in operation S542.

Operations S541 and S542 will now be described in detail with reference to FIGS. 8A through 8D.

Figure 8A:
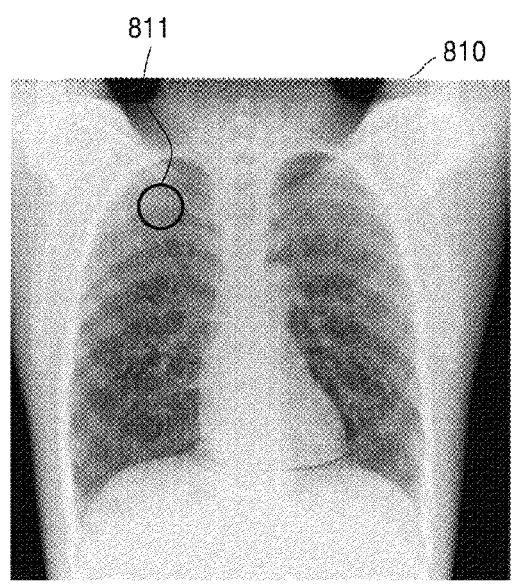
FIG. 8A is a view illustrating a medical image corresponding to when an object has an abnormality.
Figure 8B:
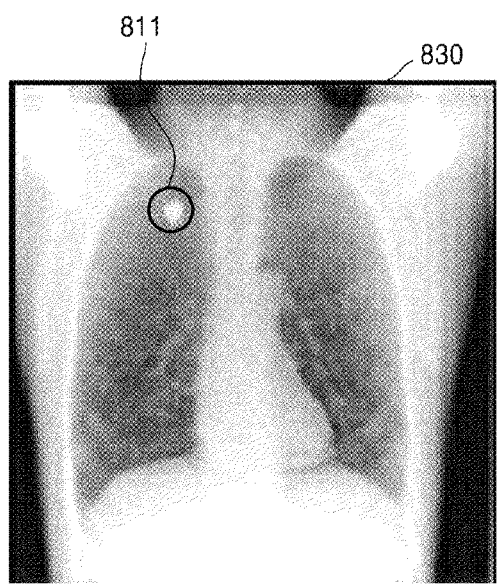
FIGS. 8B through 8D are views illustrating read assistance images generated when an object has an abnormality.
Figure 8C:
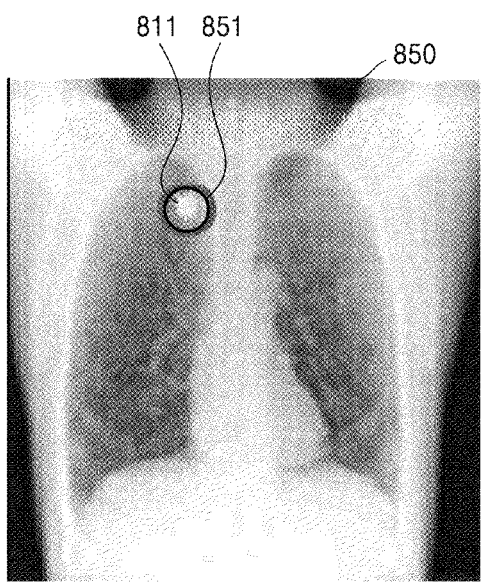
Figure 8D:
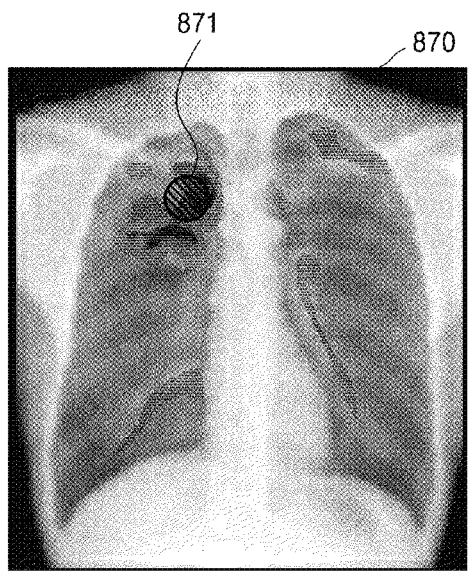

FIG. 8A is a view illustrating a medical image corresponding to when an object has an abnormality. FIGS. 8B through 8D are views illustrating read assistance images generated when the object has an abnormality.

Referring to FIG. 8A, a case where a lesion is generated in a chest may be illustrated as the case where the object has an abnormality, and an X-ray image 810 may be an original medical image.

FIGS. 8B, 8C, and 8D respectively illustrate a bone suppression image 830 obtained based on the X-ray image 810, a lesion-detected CAD image 850 obtained based on the X-ray image 810, and an abnormality map 870 obtained based on the X-ray image 810. All of the images illustrated in FIGS. 8B, 8C, and 8D may be images obtained by processing the X-ray image 810. In detail, the images illustrated in FIGS. 8B, 8C, and 8D may be obtained by inputting the X-ray image 810 to the input layer 730 of the DNN 720 and performing a learning operation on the input X-ray image 810 and output by the output layer 750.

Referring to FIG. 8A, when a lesion 811 is detected from the X-ray image 810, which is a medical image, it may be determined that the object has an abnormality.

When the object has an abnormality, the medical imaging apparatus 300 may generate at least one read assistance image, for example, the bone suppression image 830, the lesion-detected CAD image 850, and the abnormality map 870, by using the X-ray image 810, which is the medical image.

Referring to FIG. 8B, the bone suppression image 830 is an image on which an organ existing in the chest is more clearly shown by removing bones existing in the chest, including breast bones. The bone suppression image 830 may be obtained via the above-described operation based on the DNN 720. The bone suppression image 830 may be obtained via the CAD operation. Breast bones that hide the lesion 811 have been removed from the bone suppression image 830. Accordingly, a doctor may more accurately observe the lesion 811 by using the bone suppression image 830.

Referring to FIG. 8C, the lesion-detected CAD image 850 is an image on which a lesion existing in the object is detected via a CAD operation and displayed. The lesion-detected CAD image 850 puts a mark 851 on an object part having the lesion 811 such that the doctor may ascertain existence of the lesion 811 at a glance.

Referring to FIG. 8D, the abnormality map 870 is an image on which an abnormal part of a tissue or detailed areas included in the object is detected and classified as at least one stage and displayed. The abnormality map 870 displays a part 871 having a lesion differently from a normal object part such that the doctor may easily check an abnormal part of the object and the degree of the abnormality.

Referring back to FIG. 5A, in the medical image transmitting method 500, the at least one read assistance image generated in operation S542 is transmitted to the external apparatus 390, together with the medical image, in operation S543. Operation S543 may be performed by the communicator 320 under the control of the controller 310.

In the medical image transmitting method 500, at least one of the obtained medical image and the obtained at least one read assistance image may be displayed or stored, in operation S550.

In detail, when the object is normal, no read assistance images are generated, and thus the memory 350 may store only the medical image. When the object is normal, the display 340 may display only the medical image, except for the read assistance image.

On the other hand, when the object is abnormal, a medical image and at least one read assistance image are generated, and thus the memory 350 may store the medical image and the at least one read assistance image. When the object is abnormal, the display 340 may display the medical image and the at least one read assistance image.

Figure 5B:
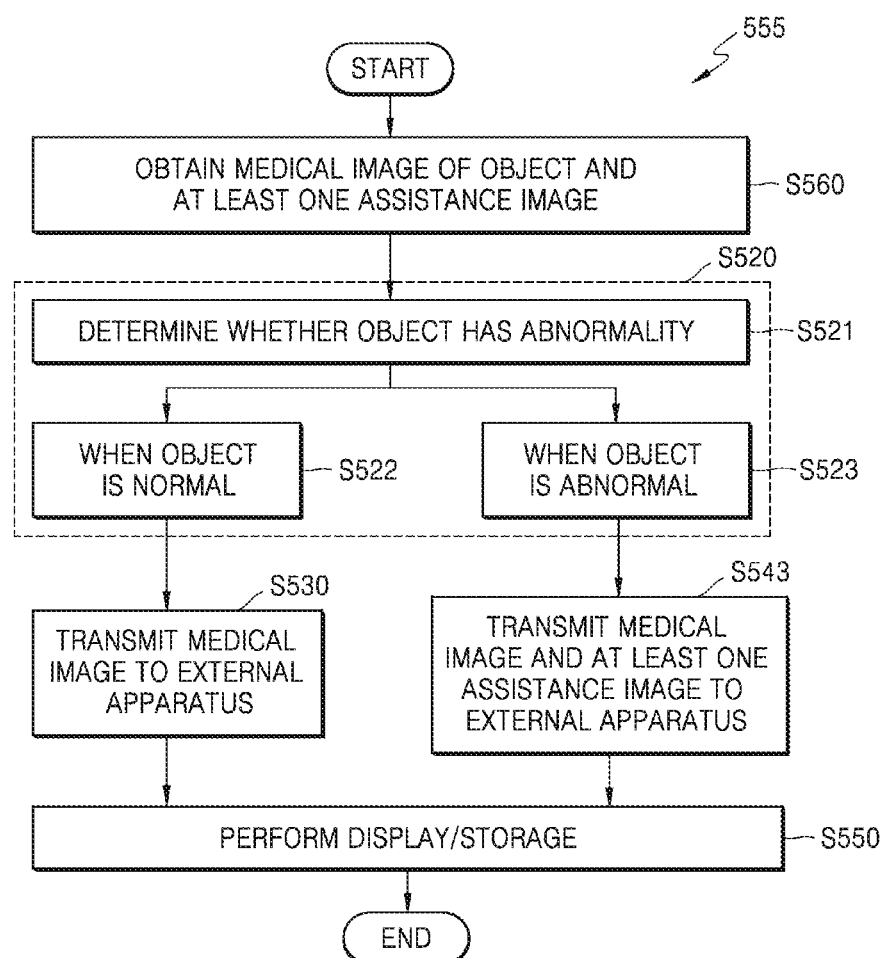
FIG. 5B is a flowchart of a medical image transmitting method according to another embodiment.

FIG. 5B is a flowchart of a medical image transmitting method 555 according to another embodiment. Operations of FIG. 5B that are the same as operations described above with reference to FIG. 5A are indicated by the same reference numerals, and thus a repeated description of the medical image transmitting method 500 given above with reference to FIG. 5A is omitted in the description of the medical image transmitting method 555 of FIG. 5B.

Referring to FIG. 5B, in the medical image transmitting method 555, a medical image and at least one read assistance image associated with the medical image may be obtained, in operation S560. In detail, in the medical image transmitting method 555, the at least one read assistance image associated with the medical image may be obtained regardless of whether the object has an abnormality. In detail, in the medical image transmitting method 555, the medical image and the at least one read assistance image associated with the medical image may be obtained before determining whether the object has an abnormality. Operation S560 may be performed under the control of the controller 310.

In operation S520, it is determined whether the object has an abnormality, based on the medical image received in operation S560, and it is determined, based on the determination, whether to transmit the at least one read assistance image associated with the medical image.

When it is determined in operation S521 that the object is normal (case S522), the medical image except for the read assistance image is transmitted to an external apparatus, in operation S530. On the other hand, when it is determined that the object is abnormal (case S523), both the medical image and the at least one read assistance image are transmitted to the external apparatus, in operation S543.

In the medical image transmitting method 555, at least one of the obtained medical image and the obtained at least one read assistance image may be displayed or stored, in operation S550.

FIG. 5C is a flowchart of a medical image transmitting method 570 according to another embodiment.

Referring to FIG. 5C, in the medical image transmitting method 570, a medical image of an object may be obtained, in operation S510.

In the medical image transmitting method 570, at least one read assistance image associated with the medical image obtained in operation S510 may be generated based on the obtained medical image, regardless of whether the object has an abnormality, in operation S580. In detail, in the medical image transmitting method 570, the at least one read assistance image associated with the medical image may be obtained before determining whether the object has an abnormality. Operation S580 may be performed under the control of the controller 310. Operation S580 corresponds to operation S542 of FIG. 5A, and thus a detailed description thereof will be omitted.

Thereafter, in operation S520, it is determined whether the object has an abnormality, based on the medical image received in operation S510, and it is determined, based on the determination, whether to transmit the at least one read assistance image associated with the medical image.

When it is determined in operation S521 that the object is normal (case S522), the medical image except for the read assistance image is transmitted to an external apparatus, in operation S530. On the other hand, when it is determined that the object is abnormal (case S523), both the medical image and the at least one read assistance image are transmitted to the external apparatus, in operation S543.

In operation S550, at least one of the obtained medical image and the obtained at least one read assistance image may be displayed or stored, in operation S550.

As described above, in the medical image transmitting methods 400 and 500, according to embodiments, and the medical imaging apparatuses 200 and 300 performing the same, when it is determined based on the medical image that the object is normal, the read assistance image associated with the medical image is not transmitted to an external apparatus, thereby preventing unnecessary transmission and generation of data. In other words, when the object has no abnormalities, unnecessary generation and/or transmission of the read assistance image may be prevented. Accordingly, a workflow of medical image reading may be optimized, and a doctor or the like does not need to unnecessarily read a read assistance image, thereby increasing reading efficiency.

In the medical image transmitting method 500 according to an embodiment and the medical imaging apparatus 300 performing the same, when the object has an abnormality, a plurality of read assistance images associated with a medical image may be generated, and may be arranged in a certain order, based on the characteristics of an abnormal part of the object. The medical image, and the plurality of read assistance images arranged in the certain order may be transmitted to the external apparatus 390. This operation may be performed under the control of the controller 310. In the medical image transmitting method 500, the arrangement operation may be performed after operation S542.

In detail, the medical imaging apparatus 300 may detect abnormality characteristics by analyzing the medical image. The abnormality characteristics are characteristic information representing an abnormal part, and thus may include the type of a disease, a location thereof, the probability that the abnormal part is a disease, a progress of the disease, a progress stage thereof, and/or the reliability of the characteristic information. The read assistance images may be arranged such that an image clearly showing these abnormality characteristics may be arranged in an order of priority.

For example, when the medical imaging apparatus 300 analyzes the medical image and detects lung pneumothorax, the abnormality characteristics may include the size of the lung pneumothorax and information of a location of the lung pneumothorax within the object.

The medical imaging apparatus 300 may arrange the plurality of read assistance images, in an order of images more clearly showing an abnormal part of the object, in detail, a detected disease, based on the abnormality characteristics.

In detail, referring to FIGS. 8A through 8D, when the lesion 811 is detected from the object as a result of analyzing the medical image 810, the plurality of read assistance images may be arranged such that a read assistance image clearly showing the lesion 811 is prioritized. For example, the bone suppression image 830, the lesion-detected CAD image 850, and the abnormality map 870 may be generated as the read assistance images associated with the medical image 810. Because the lesion 811 is the most clearly shown on the bone suppression image 830, which is a bone-removed image, the bone suppression image 830 may be arranged at a top priority, the lesion-detected CAD image 850 on which the lesion 811 is the next most clearly shown may be arranged next to the bone suppression image 830, and the abnormality map 870 may be arranged last.

As another example, when the possibility of a disease is included as the abnormality characteristic information, the plurality of the read assistance images may be arranged such that an image clearly showing an object part highly likely to be a disease may be prioritized. For example, when a plurality of portions or body parts of the object have abnormalities as a result of analyzing the medical image, a read assistance image clearly showing a part the most highly likely to be a disease may be arranged at a top priority, and a read assistance image clearly showing a part the second most highly likely to be a disease may be arranged at a next top priority.

When the object has a certain lesion, the medical imaging apparatus 300 may select the type of a read assistance image to be generated, based on abnormality characteristics, which are characteristics of the lesion. This selection may be performed by the controller 310. The above-described operation of detecting abnormality characteristics may be performed via the above-described operation based on a neural network.

In detail, when the object has a certain lesion, the controller 310 may determine the type of a read assistance image to be generated, based on the characteristics of the lesion, and may generate at least one read assistance image according to the determined type. For example, the controller 310 may select the type of a read assistance image capable of clearly showing a lesion, and may control a read assistance image of the selected type to be generated.

Figure 9:
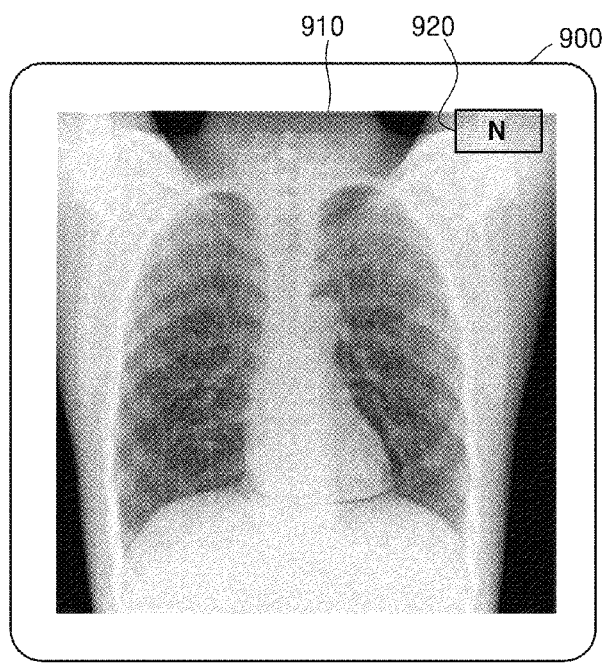
FIG. 9 is a view illustrating a user interface (UI) screen generated in an apparatus and a method, according to an embodiment.

FIG. 9 is a view illustrating a UI screen generated in an apparatus and a method according to an embodiment.

The medical imaging apparatus 300 according to an embodiment may generate a medical image including information indicating that an object is normal or abnormal, such that a medical image corresponding to when the object has an abnormality and is accordingly abnormal may be distinguished from a medical image corresponding to when the object has no abnormalities and is accordingly normal, according to whether the object has an abnormality.

In detail, when the object has no abnormalities, the medical imaging apparatus 300 may attach a normality mark indicating that the object is normal to the medical image. In detail, the controller 310 may control a medical image having the normality mark attached thereto to be generated. The normality mark is information indicating that no abnormal parts have been detected from the object, and may be expressed using at least one of a character, a symbol, and a color. Although expressed as a 'mark', this mark means all signs that distinguish normality from abnormality. For example, a case where the object is normal and a case where the object is abnormal may be distinguished from each other by differentiating the contour color of a medical image.

Referring to FIG. 9, when no abnormal parts have been detected from an object as a result of analyzing a medical image 910 of the object and thus the medical imaging apparatus 300 determines that the object is normal, the medical imaging apparatus 300 may generate a medical image 910 having a normality mark 'N' 920 attached thereto. The illustrated normality mark 'N' 920 is a mark indicating 'Normal'.

When the object is normal, the medical imaging apparatus 300 may transmit the medical image 910 having the normality mark 'N' 920 attached thereto to the external apparatus 390.

When the object has no abnormalities, the medical imaging apparatus 300 may generate data corresponding to a first UI screen 900 including the medical image 910 except for a read assistance image. The communicator 320 of the medical imaging apparatus 300 may transmit data corresponding to the first UI screen 900 to the external apparatus 390 under the control of the controller 310. Then, a display (not shown) of the external apparatus 390 may display the first UI screen 900.

The medical imaging apparatus 300 may display the medical image 910 or the first UI screen 900 on the display 340.

As described above, when it is determined via analysis of the medical image 910 that the object is normal, the medical imaging apparatus 300 according to an embodiment may generate no read assistance images, and may neither transmit any read assistance image to the external apparatus 390 nor display any read assistance image on the display 340.

In other words, a user, such as a doctor, may easily and quickly ascertain that the object is normal, by checking the normality mark 'N' 920 via the first UI screen 900 displayed on a display. When it is determined that the object is normal, the user, such as a doctor, does not spend time to read a read assistance image, thereby increasing the reading efficiency and diagnosis efficiency.

Figure 10:
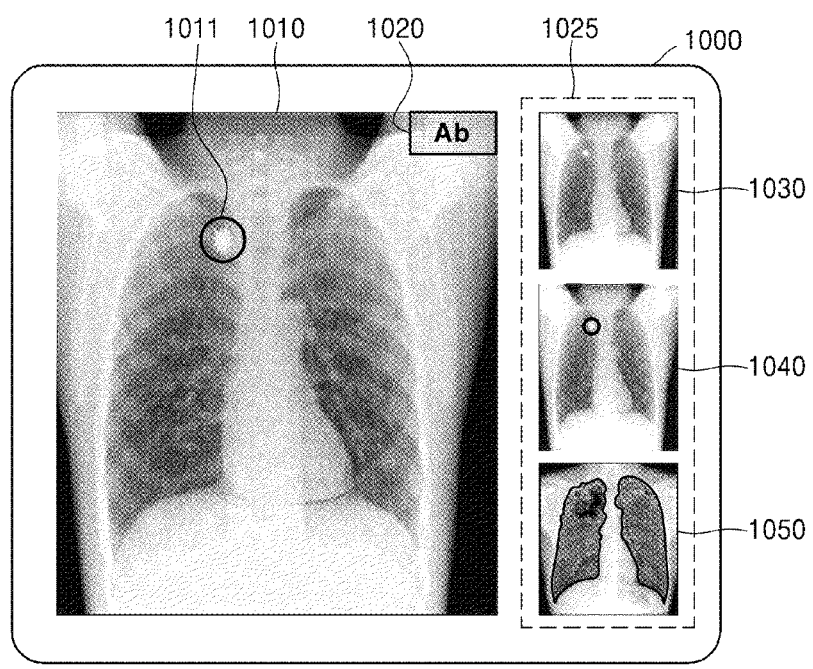
FIG. 10 is another view illustrating a UI screen generated in an apparatus and a method, according to an embodiment.

FIG. 10 is another view illustrating a UI screen generated in an apparatus and a method according to an embodiment.

Referring to FIG. 10, when the object has an abnormality, the medical imaging apparatus 300 according to an embodiment may attach an abnormality mark 'Ab' 1020 indicating that the object is abnormal, to a medical image 1010. In detail, the controller 310 may control a medical image having an abnormality mark attached thereto to be generated. The abnormality mark is information indicating that at least one abnormal part has been detected from the object. Similar to the normality mark, the abnormality mark may be expressed using at least one of a character, a symbol, and a color.

FIG. 10 illustrates a case where a lesion 1011 is detected from the object and accordingly it is determined that the object is abnormal.

Referring to FIG. 10, when the medical imaging apparatus 300 determines that the object is abnormal because an abnormal part has been detected from the object as a result of analyzing the medical image 910, which is an image of the object, the medical imaging apparatus 300 may generate a medical image 1010 having the abnormality mark 'Ab' 1020 attached thereto. The illustrated abnormality mark 'Ab' 1020 is a mark indicating 'Abnormal'.

When the object is abnormal, the medical imaging apparatus 300 may transmit the medical image 1010 having the abnormality mark 'Ab' 1020 attached thereto, together with one or more read assistance images 1030, 1040, and 1050, to the external apparatus 390.

When the object has an abnormality and thus it is determined that the object is abnormal, the medical imaging apparatus 300 may generate data corresponding to a second UI screen 1000 including the medical image 1010 and the read assistance images 1030, 1040, and 1050. The communicator 320 of the medical imaging apparatus 300 may transmit data corresponding to the second UI screen 1000 to the external apparatus 390 under the control of the controller 310. Then, the display (not shown) of the external apparatus 390 may display the second UI screen 1000.

The medical imaging apparatus 300 may display the medical image 1010 or the second UI screen 1000 on the display 340.

Figure 11:
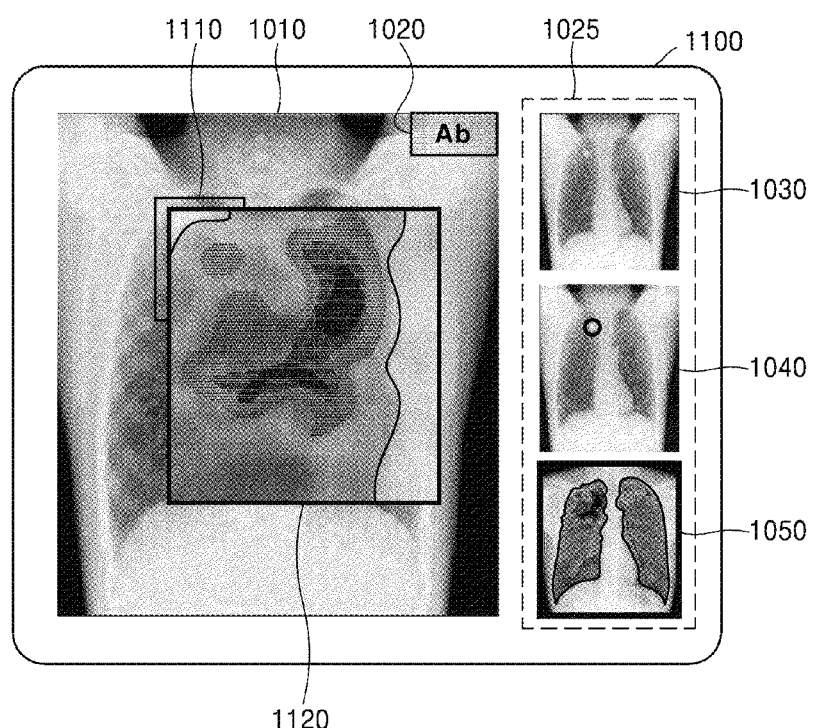
FIG. 11 is another view illustrating a UI screen generated in an apparatus and a method, according to an embodiment.

FIG. 11 is another view illustrating a UI screen generated in an apparatus and a method according to an embodiment.

Referring to FIG. 11, a UI screen 1100 includes the medical image 1010 and the plurality of read assistance images 1030, 1040, and 1050 included in the second UI screen 1000 of FIG. 10.

The medical imaging apparatus 300 according to an embodiment may display the UI screen 1100 on the display 340. The medical imaging apparatus 300 according to an embodiment may receive a manipulation, input, or request of a user via the UI unit 360.

In detail, in response to a selection input of selecting one of the plurality of read assistance images 1030, 1040, and 1050 displayed on the UI screen 1100, the controller 310 may control the selected read assistance image to be displayed on a main screen area on which the medical image 1010 is displayed.

The medical imaging apparatus 300 may receive an input of setting a region of interest (ROI) on the medical image 1010 displayed on the UI screen 1100. Then, the medical imaging apparatus 300 may magnify and display the ROI set on the medical image 1010. For example, the user may set a part of the object having the lesion as an ROI and thus may precisely observe the part having the lesion.

The medical imaging apparatus 300 may receive the selection input of selecting one of the plurality of read assistance images 1030, 1040, and 1050 displayed on the UI screen 1100, and then may receive the input of setting an ROI on the medical image 1010.

For example, the UI unit 360 may include a mouse that is used to select or set a certain part on the UI screen 1100. The user may input or select certain data by manipulating the mouse. In the above example, the user may select the read assistance image 1050, which is an abnormality map, from the plurality of read assistance images 1030, 1040, and 1050 displayed on the UI screen 1100, by using the mouse, and then may subsequently set an ROI 1110 on the medical image 1010.

Then, the medical imaging apparatus 300 may overlap an image 1120 obtained by magnifying a portion corresponding to the ROI 1110 in the abnormality map 1050, which is the selected read assistance image, on the medical image 1010 and may display a result of the overlapping.

Accordingly, the user may magnify and view a portion having a lesion from a read assistance image, thereby facilitating a diagnosis of the lesion.

Figure 12A:
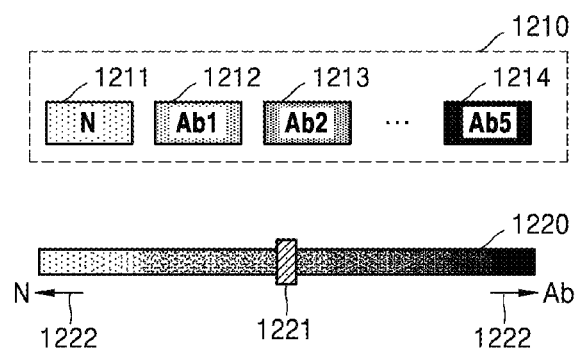
FIGS. 12A and 12B are other views illustrating UI screens generated in an apparatus and a method, according to an embodiment.
Figure 12B:
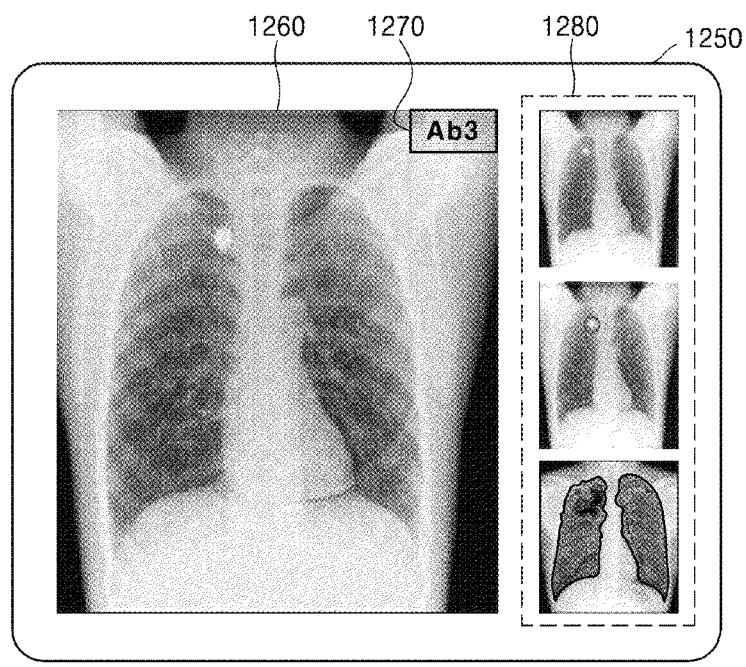

FIGS. 12A and 12B are other views illustrating UI screens generated in an apparatus and a method according to an embodiment.

Referring to FIG. 12A, when it is determined via analysis of a medical image that an object has an abnormality, the medical imaging apparatus 300 according to an embodiment may classify the abnormality of an abnormal part of the object into a plurality of stages 1210. For example, the medical imaging apparatus 300 may classify a normal case as a normal (N) stage 1211, which is a single stage, and may classify an abnormal case as one stage from among five stages, which are Ab1 (Abnormal 1) through Ab5 (Abnormal 5) stages 1212, 1213, through to 1214.

In other words, an abnormality mark displayed may be classified into a single stage from among a plurality of stages, according to the analysis of the abnormality of an abnormal part of the object, and the abnormality classification may be displayed.

In detail, the plurality of stages may be set or defined based on the size of the abnormal part, the progress of a disease, which is present in the abnormal part, and the seriousness of the disease, which is present in the abnormal part.

Alternatively, the medical imaging apparatus 300 may match the plurality of stages with a plurality of color levels or a plurality of gray levels, and may reflect a matched color in a medical image. For example, in a color bar 1220 including the plurality of gray levels or the plurality of color levels, a brightest color may be matched to an N stage 1211, which is a normal stage, and a darkest color may be matched to an Ab5 stage 1214, which is a stage having a highest abnormality. In another example, each stage could be set to have a specific color, such as red, orange, green, blue, etc., so that a user can quickly determine the stage by merely viewing the specific color that is displayed.

The medical imaging apparatus 300 may display an abnormality of an abnormal part detected from a current medical image, by using a marker 1221 on the color bar 1220. In other words, when an abnormality stage corresponds to a certain color, the medical imaging apparatus 300 may display the marker 1221 on a portion of the color bar 1220 where the certain color is located.

The plurality of stages indicating the degree of normality or abnormality may be expressed using at least one of a character, a symbol, and a color, or a combination thereof.

Referring to FIG. 12B, a UI screen 1250 corresponds to a case where the object has an abnormality. The UI screen 1250 includes a medical image 1260 and a plurality of read assistance images 1280. The medical imaging apparatus 300 may display a marker 1270 indicating the stage of the abnormality of an abnormal part of the object, on the medical image 1260. Accordingly, the user may quickly ascertain a progress stage of a disease of the object or the seriousness thereof from the medical image 1260.

Figure 13:
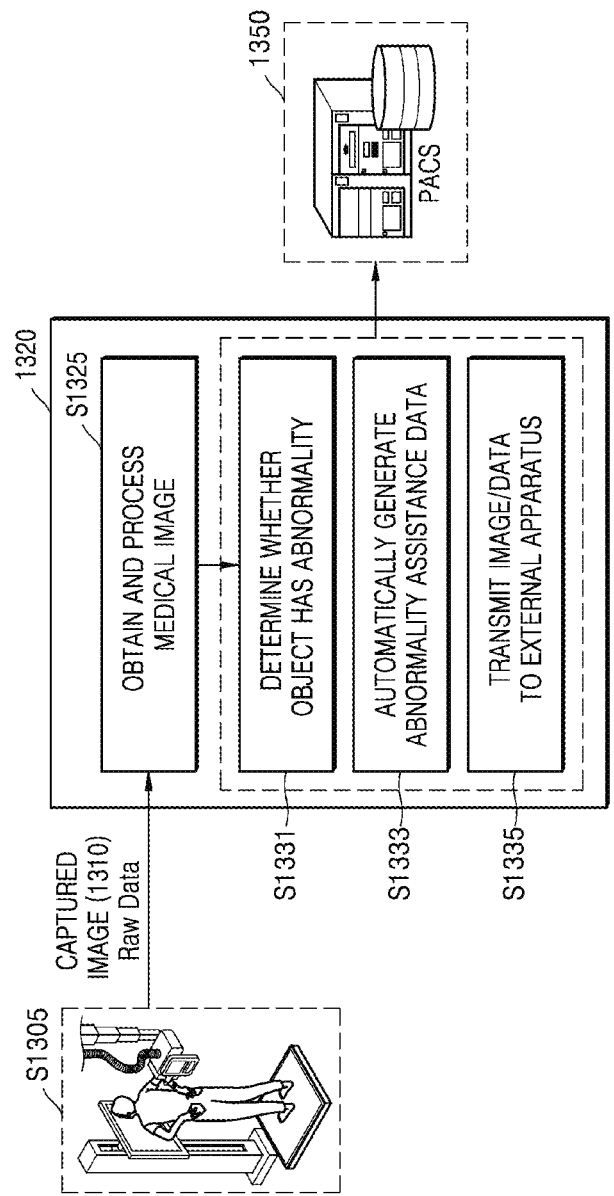
FIG. 13 is a block diagram illustrating an implementation of a medical imaging apparatus according to an embodiment.

FIG. 13 is a block diagram illustrating an implementation of a medical imaging apparatus according to an embodiment.

The medical imaging apparatus 300 according to an embodiment may be mounted on a workstation (for example, the workstation 180 of the X-ray apparatus 100) or a console of an apparatus that captures a medical image, for example, the X-ray apparatus 100 of FIG. 1, a CT apparatus, an MRI system, or an ultrasound diagnosis apparatus. A medical imaging apparatus 1320 of FIG. 13 may correspond to the above-described workstation (for example, the workstation 180 of the X-ray apparatus 100) or the above-described console.

The medical image transmitting method 500 according to an embodiment may be performed by the medical imaging apparatus 1320 of FIG. 13.

Referring to FIG. 13, the medical imaging apparatus 1320 may receive data including a captured image or raw data 1310 obtained by performing medical image capturing in operation S1305, and may obtain a medical image, based on the received data, in operation S1325. In operation S1331, the medical imaging apparatus 1320 may determine based on the medical image whether the object has an abnormality. When it is determined that the object has an abnormality and is thus classified as an abnormal state, the medical imaging apparatus 1320 may automatically generate abnormality read assistance data including information indicating abnormality characteristics and/or at least one read assistance image, in operation S1333. In operation S1335, the medical imaging apparatus 1320 may automatically transmit the generated data to the external apparatus 390, for example, a PACS server 1350.

Figure 14:
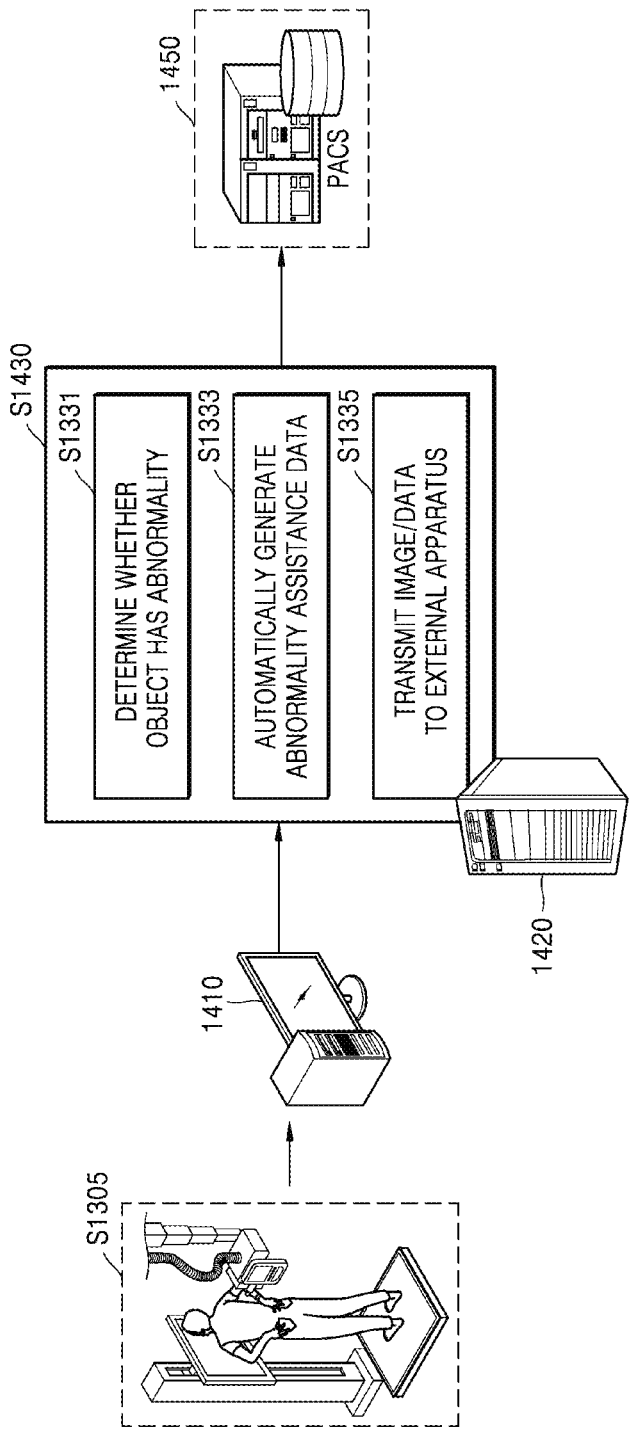
FIG. 14 is a block diagram illustrating another implementation of a medical imaging apparatus according to an embodiment.

FIG. 14 is a block diagram illustrating another implementation of a medical imaging apparatus according to an embodiment. Components of FIG. 14 that are the same as the components of FIG. 13 are indicated by the same reference numerals or characters. Thus, a repeated description thereof is omitted in the description of the components illustrated in FIG. 14.

The medical imaging apparatus 300 according to an embodiment may be mounted on a special apparatus or server independent from an apparatus that captures a medical image, for example, the X-ray apparatus 100 of FIG. 1, a CT apparatus, an MRI system, or an ultrasound diagnosis apparatus. For example, a medical imaging apparatus 1420 of FIG. 14 may be mounted on a workstation for analysis, an external medical apparatus, a PACS viewer, an external medical server, or a hospital server.

The medical image transmitting method 500 according to an embodiment may be performed by the medical imaging apparatus 1420 of FIG. 14.

In detail, when a workstation 1410 corresponds to the workstation 180 of the X-ray apparatus 100 of FIG. 1, the workstation 1410 may transmit a medical image obtained via medical image capturing to the medical imaging apparatus 1420, which is another medical server within a hospital. Then, the medical imaging apparatus 1420 may automatically determine, based on the received medical image, whether an object is normal, and may perform an additional reading operation.

Referring to FIG. 14, the workstation 1410 of the apparatus that captures a medical image may receive data including a captured image or raw data obtained by performing medical image capturing in operation S1305, and may obtain a medical image, based on the received data. The workstation 1410 transmits the obtained medical image to the medical imaging apparatus 1420. Then, the medical imaging apparatus 1420 may perform operation S1430. In detail, in operation S1331, the medical imaging apparatus 1420 may determine based on the medical image whether the object has an abnormality. When it is determined the object has an abnormality and is thus classified as an abnormal state, the medical imaging apparatus 1420 may automatically generate abnormality read assistance data including information indicating abnormality characteristics and/or at least one read assistance image, in operation S1333. In operation S1335, the medical imaging apparatus 1420 may automatically transmit the generated data to the external apparatus 390, for example, a PACS server 1450.

When the workstation 1410 corresponds to the workstation 180 of the X-ray apparatus 100 of FIG. 1, the workstation 1410 may immediately transmit a medical image obtained via medical image scanning to the external apparatus 390, for example, the PACS server 1450. The medical imaging apparatus 1420 may receive the medical image from the external apparatus 390, for example, the PACS server 1450, may perform operations S1331 and S1333, based on the received medical image, and may transmit abnormality reading assistance data generated as a result of operations S1331 and S1333 to the external apparatus 390, for example, the PACS server 1450. That is, the workstation 1410 could directly connect to the PACS server 1450, and the PACS server 1450 could directly communicate with the medical imaging apparatus 1420.

Accordingly, the external apparatus 390, for example, the PACS server 1450, may obtain the medical image and the abnormality reading assistance data and provide the obtained medical image and the obtained abnormality reading assistance data to a user, such as a doctor.

Figure 15:
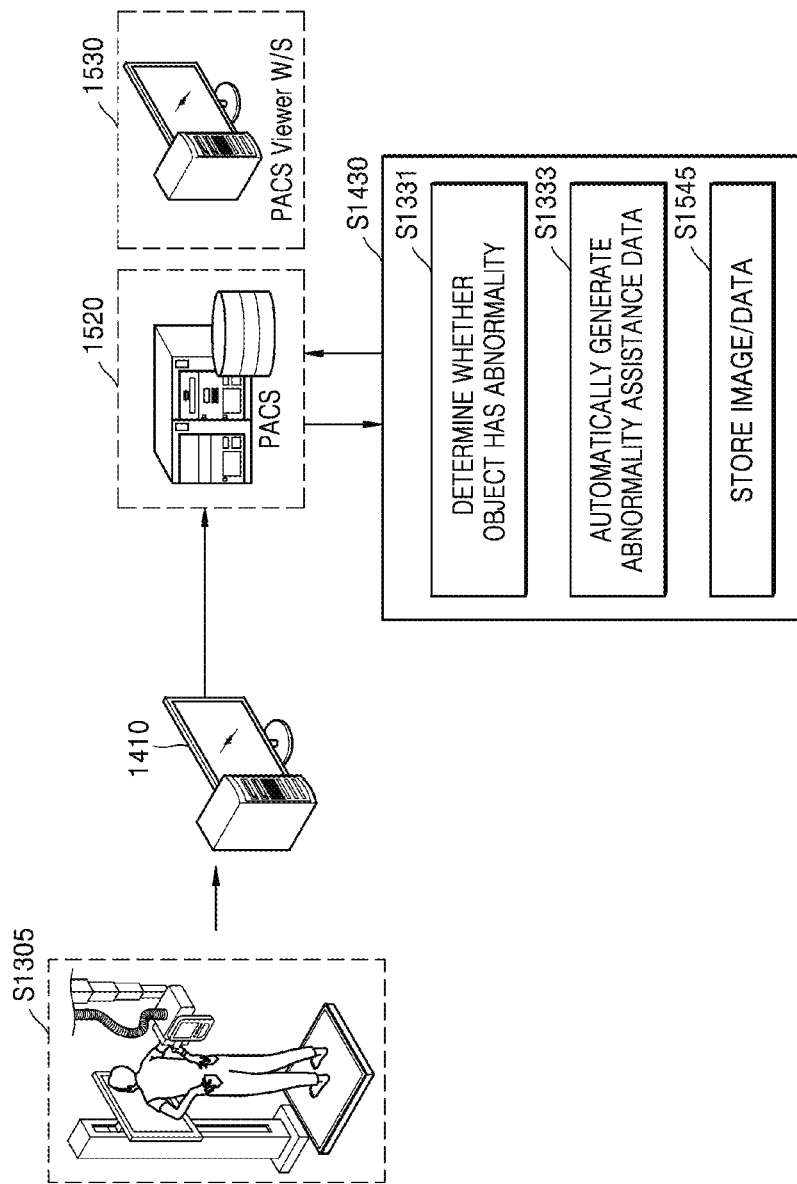
FIG. 15 is a block diagram illustrating another implementation of a medical imaging apparatus according to an embodiment.

FIG. 15 is a block diagram illustrating another implementation of a medical imaging apparatus according to an embodiment. Components of FIG. 15 that are the same as the components of FIGS. 13 and 14 are indicated by the same reference numerals or characters. Thus, a repeated description thereof is omitted in the description of the components illustrated in FIG. 15.

The medical imaging apparatus 300 according to an embodiment may be mounted on a special apparatus or server independent from an apparatus that captures a medical image, for example, the X-ray apparatus 100 of FIG. 1, a CT apparatus, an MRI system, or an ultrasound diagnosis apparatus. For example, a medical imaging apparatus 1520 of FIG. 15 may be mounted on a workstation for analysis, an external medical apparatus, a PACS server, an external medical server, or a hospital server.

The medical image transmitting method 500 according to an embodiment may be performed by the medical imaging apparatus 1520 of FIG. 15. The embodiment of FIG. 15 is different from that of FIG. 14 in that the medical imaging apparatus 1520 is an independent electronic apparatus capable of independently processing, storing, and managing medical image data, such as a PACS server, and thus autonomously may store and manage at least one read assistance image without transmitting the at least one read assistance image to another external apparatus.

Referring to FIG. 15, the workstation 1410 of the apparatus that captures a medical image may receive data including a captured image or raw data obtained by performing medical image capturing in operation S1305, and may obtain a medical image, based on the received data. The workstation 1410 transmits the obtained medical image to the medical imaging apparatus 1520, for example, a PACS server. Then, the medical imaging apparatus 1520 may perform operation S1430. In detail, in operation S1331, the medical imaging apparatus 1520 may determine based on the medical image whether the object has an abnormality. When it is determined the object has an abnormality and is thus classified as an abnormal state, the medical imaging apparatus 1520 may automatically generate abnormality read assistance data including information indicating abnormality characteristics and/or at least one read assistance image, in operation S1333. In operation S1545, the medical imaging apparatus 1520 may automatically store the generated abnormality read assistance data. The medical imaging apparatus 1520 may transmit at least one of the abnormality read assistance data obtained via operation S1430 and the medical image to a PACS viewer or a workstation 1530 connected to the PACS viewer. Then, the PACS viewer or the workstation 1530 connected to the PACS viewer may provide the received abnormality read assistance data and the received medical image to a user, such as a doctor.

FIG. 15 illustrates a case where operation S1430 of FIG. 15 is performed by the medical imaging apparatus 1520. However, operation S1430 of FIG. 15 may also be performed by the PACS viewer or the workstation 1530 connected to the PACS viewer, wherein the PACS viewer and the workstation 1530 are connected to the medical imaging apparatus 1520.

In a medical image transmitting method according to an embodiment, and a medical imaging apparatus performing the same, when it is determined based on the medical image that the object is normal, the read assistance image associated with the medical image is not transmitted to an external apparatus, thereby preventing unnecessary transmission and generation of data. Accordingly, when the object has no abnormalities, unnecessary generation and/or transmission of the read assistance image may be prevented. Accordingly, a workflow of medical image reading may be optimized, and a doctor or the like does not need to unnecessarily read a read assistance image, thereby increasing reading efficiency.

Embodiments may be implemented through non-transitory computer-readable recording media having recorded thereon computer-executable instructions and data. The instructions may be stored in the form of program codes, and when executed by a processor, generate a predetermined program module to perform a specific operation. Furthermore, when being executed by the processor, the instructions may perform specific operations according to the embodiments.

While one or more embodiments have been described with reference to the figures, it will be understood by one of ordinary skill in the art that various changes in form and details may be made therein without departing from the spirit and scope of the present disclosure as defined by the following claims.

Accordingly, the above embodiments and all aspects thereof are examples only and are not limiting.

What is claimed is:

1. A medical imaging apparatus comprising:
at least one processor; and
a communication circuitry coupled to the at least one processor and configured to communicate with an external apparatus via a communication network,
wherein the at least one processor is configured to:
obtain a medical image generated by imaging an object,
perform a first determination to automatically determine whether the object has an abnormality,
when the first determination automatically determines the object has an abnormality, generate at least one assistance image associated with the medical image, classify the abnormality as a stage from among a plurality of stages, and generate a visual abnormality information indicating the classified stage of the abnormality, wherein the visual abnormality information is displayed with the medical image,
based on the first determination, perform a second determination to identify whether to transmit, to the external apparatus via the communication network, the medical image without the at least one assistance image or both the medical image and the at least one assistance image,
in response to the identifying to transmit both the medical image and the at least one assistance image in the second determination, control the communication circuitry to transmit, to the external apparatus, the medical image, the at least one assistance image, and the visual abnormality information indicating the classified stage of the abnormality, and
in response to the identifying to transmit the medical image without transmitting the at least one assistance image in the second determination, control the communication circuitry to transmit, to the external apparatus, the medical image,
wherein the second determination identifies to transmit the medical image without transmitting the at least one assistance image based on determining that the object does not have an abnormality in the first determination, and identifies to transmit the medical image, the at least one assistance image, and the visual abnormality information based on determining that the object has an abnormality in the first determination,
wherein the classified stage of abnormality is one of a plurality of stages defined based on size of the abnormality, progress of a disease in the abnormality, and seriousness of the disease in the abnormality,
wherein the visual abnormality information indicating the classified stage of the abnormality includes displaying a marker on a color bar having colors corresponding to the plurality of stages.

2. The medical imaging apparatus of claim 1, wherein, based on the determining that the object has no abnormalities, the at least one processor is further configured to:
attach, to the medical image, a normality mark indicating that the object is normal, and
control the communication circuitry to transmit, to the external apparatus, the medical image to which the normality mark has been attached.

3. The medical imaging apparatus of claim 1, wherein, based on the determining that the object has the abnormality, the at least one processor is further configured to:
attach, to the medical image, an abnormality mark indicating that the object is abnormal, and
control the communication circuitry to transmit, to the external apparatus, the medical image to which the abnormality mark has been attached.

4. The medical imaging apparatus of claim 1,
wherein the at least one assistance image is at least two assistance images associated with the medical image,
wherein, based on the determining that the object has the abnormality, the at least one processor is further configured to:
arrange the at least two assistance images in a certain order, based on characteristics of an abnormal part of the object, and
control the communication circuitry to transmit the medical image and the at least two assistance images arranged in the certain order to the external apparatus.

5. The medical imaging apparatus of claim 1, wherein, based on the object having a lesion, the at least one processor is further configured to:
based on a type of the lesion, determine a type of an assistance image to be generated, and generate the at least one assistance image according to its determined type.

6. The medical imaging apparatus of claim 1, wherein, based on the object having no abnormalities, the at least one processor is further configured to control generation of data corresponding to a first user interface (UI) screen comprising the medical image;
  wherein, based on the object having the abnormality, the at least one processor is further configured to control generation of data corresponding to a second UI screen comprising the medical image and the at least one assistance image; and
  wherein the at least one processor is further configured to control the communication circuitry to transmit the data corresponding to the first UI screen or the data corresponding to the second UI screen to the external apparatus.

7. The medical imaging apparatus of claim 1, wherein, based on the object having no abnormalities, the at least one processor is further configured to control generation of data corresponding to a first user interface (UI) screen comprising the medical image;
  wherein, based on the object having the abnormality, the at least one processor is further configured to control generation of data corresponding to a second UI screen comprising the medical image and the at least one assistance image; and
  wherein the medical imaging apparatus further comprises a display configured to display the first UI screen or the second UI screen under the control of the at least one processor.

8. The medical imaging apparatus of claim 1, wherein the at least one processor is further configured to perform the first determination to determine whether the object has the abnormality, via a deep neural network (DNN) processor configured to perform learning operations via a DNN.

9. The medical imaging apparatus of claim 1, further comprising an X-ray radiator configured to radiate X-rays to the object,
  wherein the at least one processor is further configured to control the X-ray radiator to obtain the medical image.

10. The medical imaging apparatus of claim 1, wherein, in the first determination, the at least one processor is further configured to:
  analyze the medical image and detect a presence of a lesion in the medical image, and
  generate the at least one assistance image to include an image of the lesion and a marking indicating the presence of the lesion.

11. The medical imaging apparatus of claim 5, wherein the at least one processor is configured to:
  based on the type of the lesion corresponding to a lesion located in a soft tissue included in the object, generate the at least one assistance image as a bone suppression image.

12. The medical imaging apparatus of claim 1, wherein the at least one processor is further configured to generate the at least one assistance image based on the medical image by an image generating method which is different from an image generating method by which the medical image was generated.

13. The medical imaging apparatus of claim 1, wherein the visual abnormality information comprises a marker indicating the classified stage of the abnormality, and the marker is located on the medical image.

14. The medical imaging apparatus of claim 1,
  wherein the at least one assistance image is at least one read assistance mage that is based on the medical image and depicts the abnormality more clearly than the medical image; and
  wherein the second determination identifying to transmit the medical image, the at least one assistance image, and the visual abnormality information includes, in response to determining that the object has the abnormality in the first determination:
    requesting a user input from a user interface regarding the at least one read assistance image, and
    receiving the user input from the user interface.

* * * * *